(12) United States Patent
Lowe et al.

(10) Patent No.: US 7,799,566 B2
(45) Date of Patent: Sep. 21, 2010

(54) CYCLIN D POLYNUCLEOTIDES, POLYPEPTIDES AND USES THEREOF

(75) Inventors: Keith S. Lowe, Johnston, IA (US); Yumin Tao, Fremont, CA (US); William J. Gordon-Kamm, Urbandale, IA (US); Carolyn A. Gregory, Tega City, SC (US); John A. McElver, Durham, NC (US); George J. Hoerster, Des Moines, IA (US); Sheila E. Maddock, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 754 days.

(21) Appl. No.: 11/560,550

(22) Filed: Nov. 16, 2006

(65) Prior Publication Data

US 2008/0242624 A1  Oct. 2, 2008

Related U.S. Application Data

(60) Continuation of application No. 10/348,110, filed on Jan. 21, 2003, now abandoned, which is a division of application No. 09/398,858, filed on Sep. 20, 1999, now Pat. No. 6,518,487.

(60) Provisional application No. 60/101,551, filed on Sep. 23, 1998.

(51) Int. Cl.
*C12N 15/82* (2006.01)
*C12N 15/29* (2006.01)
*A01H 4/00* (2006.01)

(52) U.S. Cl. .................. 435/468; 435/419; 435/320.1; 435/252.3; 536/23.6

(58) Field of Classification Search .............. None
See application file for complete search history.

(56) References Cited

U.S. PATENT DOCUMENTS

| 5,514,571 | A | 5/1996 | Riabowol |
| 6,066,501 | A | 5/2000 | Beach |
| 6,087,175 | A | 7/2000 | John |
| 6,166,293 | A | 12/2000 | Doerner et al. |
| 6,559,358 | B1 * | 5/2003 | Murray .................. 800/290 |

FOREIGN PATENT DOCUMENTS

| WO | 92/09685 A1 | 6/1992 |
| WO | 92/20796 A2 | 11/1992 |
| WO | 98/03631 A1 | 1/1998 |
| WO | 98/42851 A1 | 10/1998 |
| WO | 99/22002 A1 | 5/1999 |
| WO | 99/48486 A2 | 9/1999 |

OTHER PUBLICATIONS

Sherr C.J. D-type cyclins. Trends Biochem Sci. May 1995;20(5):187-190.*
Wang et al., Mammary hyperplasia and carcinoma in MMTV-cyclin D1 transgenic mice, Nature (1994) 369:669-671.
Soni et al., A Family of Cyclin D Homologs from Plants Differentially Controlled by Growth Regulators and Containing the Conserved Retinoblastoma Protein Interaction Motif, Plant Cell (1995) 7:85-103.
Dahl et al., The D-Type Alfalfa Cyclin Gene cycMs4 Complements G1 Cyclin-Deficient Yeast and Is Induced in the G1 Phase of the Cell Cycle, Plant Cell (1995) 7:1847-1857.
Hyman et al., *Plasmodium falciparum* chromosome 12 clone 3D7, EBI Database Accession No. AC005506 (1998).
Renz et al., C.rubrum mRNA for cycline-D like protein, EBI Database Accession No. Y10162 (1997).
Bell et al., Tobacco plants transformed with cdc25, a mitotic inducer gene from fission yeast, Plant Molecular Biology (1993) 23:445-451.
Sun et al., Alternative splicing of cyclin transcripts in maize endosperm, Gene (1997) 195:167-175.
Renaudin et al., Plant cyclins: a unified nomenclature for Plant A-, B- and D-type cyclins based on sequence organization, Plant Molecular Biology (1996) 32:1003-1018.
Riou-Khamlichi et al., Cytokinin Activation of *Arabidopsis* Cell Division Through a D-Type Cyclin, Science (1999) 283:1541-1544.
Daidoji et al., Proliferating Cell Nuclear Antigen (PCNA/Cyclin) in Plant Proliferating Cells: Immunohistochemical and Quantitative Analysis using Autoantibody and Murine Monoclonal Antibodies to PCNA, Cell Biochemistry and Function (1992) 10:123-132.
Tao et al., Maize D-type cyclin genes and their potential for improving transformation, In Vitro Cellular and Developmental Biology Animal (2000) vol. 36, No. 3, Part 2, p. 33-A.
Cockcroft et al., Cyclin D control of growth rate in Plants, Nature (2000) 405(6786):575-579.

* cited by examiner

*Primary Examiner*—Cynthia Collins

(57) ABSTRACT

The invention provides isolated polynucleotides, specifically Cyclin D polynucleotides, and their encoded proteins that are involved in cell cycle regulation. The invention further provides recombinant expression cassettes, host cells, transgenic plants, and antibody compositions. The present invention provides methods and compositions relating to altering cell cycle protein content and/or composition of plants for the purpose of increasing transformation efficiency.

12 Claims, No Drawings

SEQUENCE LISTING

```
<160> NUMBER OF SEQ ID NOS: 30

<210> SEQ ID NO 1
<211> LENGTH: 1861
<212> TYPE: DNA
<213> ORGANISM: Zea mays
<220> FEATURE:
<221> NAME/KEY: CDS
<222> LOCATION: (275)...(1351)

<400> SEQUENCE: 1
tcctctgtcc tccctctcc acttgagaag aacacaatta gaaaaaaagg caaaaaacat      60
ttaccttttt tctatctgta tattatctga ataaatcaag aggaggaaga ggggagggag    120
cgagggaggg ggaggagtag caaatccaga ctccatagca accagctcgc gagaagggga    180
aaagggggag gaagagcttc gcttgtgtat tgattgctcg ctgctccagt ccctgcattc    240
gtgccgtttt tggcaagtag gtggcgtggc aagc atg gtg ccg ggc tat gac tgc    295
                                       Met Val Pro Gly Tyr Asp Cys
                                         1               5 gcc gcc tcc gtg ctg ctg tgc gcg gag gac aac gct gct att ctc ggc     343
Ala Ala Ser Val Leu Leu Cys Ala Glu Asp Asn Ala Ala Ile Leu Gly
         10                  15                  20 ctg gac gac gat ggg gag gag tcc tcc tgg gcg gcc gcc gct acg ccg     391
Leu Asp Asp Asp Gly Glu Glu Ser Ser Trp Ala Ala Ala Ala Thr Pro
     25                  30                  35 cca cgt gac acc gtc gcc gcc gcc gcc gcc acg ggg gtc gcc gtc gat    439
Pro Arg Asp Thr Val Ala Ala Ala Ala Ala Thr Gly Val Ala Val Asp
 40                  45                  50                  55 ggg att ttg acg gag ttc ccc ttg ctc tcg gat gac tgc gtt gcg acg     487
Gly Ile Leu Thr Glu Phe Pro Leu Leu Ser Asp Asp Cys Val Ala Thr
             60                  65                  70 ctc gtg gag aag gag gtg gag cac atg ccc gcg gag ggg tac ctc cag     535
Leu Val Glu Lys Glu Val Glu His Met Pro Ala Glu Gly Tyr Leu Gln
         75                  80                  85 aag ctg cag cga cgg cat ggg gac ctg gat ttg gcc gcc gtc agg aag     583
Lys Leu Gln Arg Arg His Gly Asp Leu Asp Leu Ala Ala Val Arg Lys
     90                  95                 100 gac gcc atc gat tgg att tgg aag gtc att gag cat tac aat ttc gca     631
Asp Ala Ile Asp Trp Ile Trp Lys Val Ile Glu His Tyr Asn Phe Ala
105                 110                 115 ccg ttg act gcc gtt ttg tct gtg aac tac ctc gat aga ttc ctc tcc     679
Pro Leu Thr Ala Val Leu Ser Val Asn Tyr Leu Asp Arg Phe Leu Ser
120                 125                 130                 135 acg tat gag ttc cct gaa ggc aga gct tgg atg act cag ctc ttg gca     727
Thr Tyr Glu Phe Pro Glu Gly Arg Ala Trp Met Thr Gln Leu Leu Ala
                140                 145                 150
```

```
gtg gct tgc ttg tct ttg gct tcg aaa atc gaa gag act ttt gtg cca      775
Val Ala Cys Leu Ser Leu Ala Ser Lys Ile Glu Glu Thr Phe Val Pro
            155                 160                 165 ctc ccc ttg gat ttg cag gta gcg gag gca aag ttt gtt ttt gag gga      823
Leu Pro Leu Asp Leu Gln Val Ala Glu Ala Lys Phe Val Phe Glu Gly
            170                 175                 180 agg acc ata aaa agg atg gag ctt ctg gtg cta agc acc tta aag tgg      871
Arg Thr Ile Lys Arg Met Glu Leu Leu Val Leu Ser Thr Leu Lys Trp
        185                 190                 195 agg atg cat gct gtt act gct tgc tca ttt gtt gaa tac ttt ctt cat      919
Arg Met His Ala Val Thr Ala Cys Ser Phe Val Glu Tyr Phe Leu His
200                 205                 210                 215 aaa ttg agt gat cat ggt gca ccc tcc ttg ctt gca cgc tct cgc tct      967
Lys Leu Ser Asp His Gly Ala Pro Ser Leu Leu Ala Arg Ser Arg Ser
                220                 225                 230 tcg gac ctt gtc ttg agc acc gct aaa ggt gct gaa ttc gtg gta ttc     1015
Ser Asp Leu Val Leu Ser Thr Ala Lys Gly Ala Glu Phe Val Val Phe
            235                 240                 245 aga ccc tcc gag att gct gcc agt gtt gca ctt gct gct atc ggc gaa     1063
Arg Pro Ser Glu Ile Ala Ala Ser Val Ala Leu Ala Ala Ile Gly Glu
            250                 255                 260 tgc agg agt tct gta att gag aga gct gct agt agc tgc aaa tat ttg     1111
Cys Arg Ser Ser Val Ile Glu Arg Ala Ala Ser Ser Cys Lys Tyr Leu
        265                 270                 275 gac aag gag agg gtt tta aga tgc cat gaa atg att caa gag aag att     1159
Asp Lys Glu Arg Val Leu Arg Cys His Glu Met Ile Gln Glu Lys Ile
280                 285                 290                 295 act gcg gga agc att gtc cta aag tct gct gga tca tca atc tcc tct     1207
Thr Ala Gly Ser Ile Val Leu Lys Ser Ala Gly Ser Ser Ile Ser Ser
                300                 305                 310 gtg cca caa agc cca ata ggt gtc ctg gac gct gca gcc tgt ctg agt     1255
Val Pro Gln Ser Pro Ile Gly Val Leu Asp Ala Ala Ala Cys Leu Ser
            315                 320                 325 caa caa agc gat gac gct act gtc ggg tct cct gca gta tgt tac cat     1303
Gln Gln Ser Asp Asp Ala Thr Val Gly Ser Pro Ala Val Cys Tyr His
            330                 335                 340 agt tct tcc aca agc aag agg aga agg atc act aga cgt cta ctc taa     1351
Ser Ser Ser Thr Ser Lys Arg Arg Arg Ile Thr Arg Arg Leu Leu *
        345                 350                 355 ttgtggtacg cttcaggtgt gctcctcacc gctctaggag ttttttgattg gttcaaacat  1411 cttaaattta gtttggccgc tggaggatta tggtttagtc aagtagttgc tgaatggaac   1471
aacaaaacac gcacactact tggtccataa agacaagaaa ataactggca gcgtcccgcg   1531
agccagcgct gcaatccagt tcatgcaaga ccctagagtc cagggggggt gctggtgtag   1591
gtagagaggg aacaaggcat tcacatacgc cgtagagatg agagagcctc tcgtatgttt   1651 tgtactttg ctccttcagt ttgcaatgaa ctatataaac aaggattgcc ttggggcagt    1711
gaacatttgt cggatgaaaa gaatcaaaaa ggatggggt cggcagagga atagaacaat    1771
ttgatatatt tccataaact acagatatgt ttccttttc ataatgatga gctatcattt    1831
ttgttgatgg taacaaaaaa aaaaaaaaa                                     1861

<210> SEQ ID NO 2
<211> LENGTH: 358
<212> TYPE: PRT
<213> ORGANISM: Zea mays

<400> SEQUENCE: 2
```

```
Met Val Pro Gly Tyr Asp Cys Ala Ala Ser Val Leu Cys Ala Glu
 1               5                  10                  15

Asp Asn Ala Ala Ile Leu Gly Leu Asp Asp Gly Glu Glu Ser Ser
                20                  25                  30

Trp Ala Ala Ala Thr Pro Arg Asp Thr Val Ala Ala Ala
                35              40                  45

Ala Thr Gly Val Ala Val Asp Gly Ile Leu Thr Glu Phe Pro Leu Leu
    50                  55                  60

Ser Asp Asp Cys Val Ala Thr Leu Val Glu Lys Glu Val Glu His Met
65                  70                  75                  80

Pro Ala Glu Gly Tyr Leu Gln Lys Leu Gln Arg Arg His Gly Asp Leu
                85                  90                  95

Asp Leu Ala Ala Val Arg Lys Asp Ala Ile Asp Trp Ile Trp Lys Val
                100                 105                 110

Ile Glu His Tyr Asn Phe Ala Pro Leu Thr Ala Val Leu Ser Val Asn
            115                 120                 125

Tyr Leu Asp Arg Phe Leu Ser Thr Tyr Glu Phe Pro Glu Gly Arg Ala
130                 135                 140

Trp Met Thr Gln Leu Leu Ala Val Ala Cys Leu Ser Leu Ala Ser Lys
145                 150                 155                 160

Ile Glu Glu Thr Phe Val Pro Leu Pro Leu Asp Leu Gln Val Ala Glu
                165                 170                 175

Ala Lys Phe Val Phe Glu Gly Arg Thr Ile Lys Arg Met Glu Leu Leu
                180                 185                 190

Val Leu Ser Thr Leu Lys Trp Arg Met His Ala Val Thr Ala Cys Ser
            195                 200                 205

Phe Val Glu Tyr Phe Leu His Lys Leu Ser Asp His Gly Ala Pro Ser
210                 215                 220

Leu Leu Ala Arg Ser Arg Ser Ser Asp Leu Val Leu Ser Thr Ala Lys
225                 230                 235                 240

Gly Ala Glu Phe Val Val Phe Arg Pro Ser Glu Ile Ala Ala Ser Val
                245                 250                 255

Ala Leu Ala Ala Ile Gly Glu Cys Arg Ser Ser Val Ile Glu Arg Ala
                260                 265                 270

Ala Ser Ser Cys Lys Tyr Leu Asp Lys Glu Arg Val Leu Arg Cys His
    275                 280                 285

Glu Met Ile Gln Glu Lys Ile Thr Ala Gly Ser Ile Val Leu Lys Ser
290                 295                 300

Ala Gly Ser Ser Ile Ser Ser Val Pro Gln Ser Pro Ile Gly Val Leu
305                 310                 315                 320

Asp Ala Ala Ala Cys Leu Ser Gln Gln Ser Asp Ala Thr Val Gly
                325                 330                 335

Ser Pro Ala Val Cys Tyr His Ser Ser Ser Thr Ser Lys Arg Arg Arg
                340                 345                 350

Ile Thr Arg Arg Leu Leu
            355

<210> SEQ ID NO 3
<211> LENGTH: 27
<212> TYPE: DNA
<213> ORGANISM: Zea mays
<220> FEATURE:
<221> NAME/KEY: protein_bind
<222> LOCATION: (1)...(27)

<400> SEQUENCE: 3
```

-continued

```
gcaagcatgg tgccgggcta tgactgc                                              27

<210> SEQ ID NO 4
<211> LENGTH: 30
<212> TYPE: DNA
<213> ORGANISM: Zea mays
<220> FEATURE:
<221> NAME/KEY: protein_bind
<222> LOCATION: (1)...(30)

<400> SEQUENCE: 4
agcggtgagg agcacacctg aagcgtacca                                           30

<210> SEQ ID NO 5
<211> LENGTH: 27
<212> TYPE: DNA
<213> ORGANISM: Zea mays
<220> FEATURE:
<221> NAME/KEY: primer_bind
<222> LOCATION: (1)...(27)

<400> SEQUENCE: 5
tctattcctc tgccgacccc catcctt                                              27

<210> SEQ ID NO 6
<211> LENGTH: 30
<212> TYPE: DNA
<213> ORGANISM: Zea mays
<220> FEATURE:
<221> NAME/KEY: protein_bind
<222> LOCATION: (1)...(30)

<400> SEQUENCE: 6
cccctctcca cttgagaaga acacaattag                                           30

<210> SEQ ID NO 7
<211> LENGTH: 25
<212> TYPE: DNA
<213> ORGANISM: Zea mays
<220> FEATURE:
<221> NAME/KEY: primer_bind
<222> LOCATION: (1)...(25)

<400> SEQUENCE: 7
cgggctatga ctgcgccgcc tccgt                                                25

<210> SEQ ID NO 8
<211> LENGTH: 27
<212> TYPE: DNA
<213> ORGANISM: Zea mays
<220> FEATURE:
<221> NAME/KEY: protein_bind
<222> LOCATION: (1)...(27)

<400> SEQUENCE: 8
ctcctcttgc ttgtggaaga actatgg                                              27

<210> SEQ ID NO 9
<211> LENGTH: 25
<212> TYPE: DNA
<213> ORGANISM: Zea mays
<220> FEATURE:
<221> NAME/KEY: primer_bind
<222> LOCATION: (1)...(25)

<400> SEQUENCE: 9
```

```
atggtgccgg gctatgactg cgccg                                          25
```

<210> SEQ ID NO 10
<211> LENGTH: 25
<212> TYPE: DNA
<213> ORGANISM: Zea mays
<220> FEATURE:
<221> NAME/KEY: protein_bind
<222> LOCATION: (1)...(25)

<400> SEQUENCE: 10

```
ttagagtaga cgtctagtga tcctt                                          25
```

<210> SEQ ID NO 11
<211> LENGTH: 1077
<212> TYPE: DNA
<213> ORGANISM: Zea mays
<220> FEATURE:
<221> NAME/KEY: CDS
<222> LOCATION: (1)...(1077)

<400> SEQUENCE: 11

| atg | gtg | ccg | ggc | tat | gac | tgc | gcc | gcc | tcc | gtg | ctg | ctg | tgc | gcg | gag | 48 |
| Met | Val | Pro | Gly | Tyr | Asp | Cys | Ala | Ala | Ser | Val | Leu | Leu | Cys | Ala | Glu | |
| 1 | | | | 5 | | | | | 10 | | | | | 15 | | |

| gac | aac | gct | gct | att | ctc | ggc | ctg | gac | gac | gat | ggg | gag | gag | tcc | tcc | 96 |
| Asp | Asn | Ala | Ala | Ile | Leu | Gly | Leu | Asp | Asp | Asp | Gly | Glu | Glu | Ser | Ser | |
| | | | 20 | | | | | 25 | | | | | 30 | | | |

| tgg | gcg | gcc | gcc | gct | acg | ccg | cca | cgt | gac | acc | gtc | gcc | gcc | gcc | gcc | 144 |
| Trp | Ala | Ala | Ala | Ala | Thr | Pro | Pro | Arg | Asp | Thr | Val | Ala | Ala | Ala | Ala | |
| | | 35 | | | | | 40 | | | | | 45 | | | | |

| gcc | acc | ggg | gtc | gcc | gtc | gat | ggg | att | ttg | acg | gag | ttc | ccc | ttg | ctc | 192 |
| Ala | Thr | Gly | Val | Ala | Val | Asp | Gly | Ile | Leu | Thr | Glu | Phe | Pro | Leu | Leu | |
| | 50 | | | | | 55 | | | | | 60 | | | | | |

| tcg | gat | gac | tgc | gtt | gcg | acg | ctc | gtg | gag | aag | gag | gtg | gag | cac | atg | 240 |
| Ser | Asp | Asp | Cys | Val | Ala | Thr | Leu | Val | Glu | Lys | Glu | Val | Glu | His | Met | |
| 65 | | | | 70 | | | | | 75 | | | | | 80 | | |

| ccc | gcg | gag | ggg | tac | ctc | cag | aag | ctg | cag | cga | cgg | cat | ggg | gac | ctg | 288 |
| Pro | Ala | Glu | Gly | Tyr | Leu | Gln | Lys | Leu | Gln | Arg | Arg | His | Gly | Asp | Leu | |
| | | | | 85 | | | | | 90 | | | | | 95 | | |

| gat | ttg | gtc | gcc | gtc | agg | aag | gac | gcc | atc | gat | tgg | att | tgg | aag | gtc | 336 |
| Asp | Leu | Val | Ala | Val | Arg | Lys | Asp | Ala | Ile | Asp | Trp | Ile | Trp | Lys | Val | |
| | | | 100 | | | | | 105 | | | | | 110 | | | |

| att | gag | cat | tac | aat | ttc | gca | ccg | ttg | act | gcc | gtt | tgt | tct | gtg | aac | 384 |
| Ile | Glu | His | Tyr | Asn | Phe | Ala | Pro | Leu | Thr | Ala | Val | Leu | Ser | Val | Asn | |
| | | 115 | | | | | 120 | | | | | 125 | | | | |

| tac | ctc | gat | aga | ttc | ctc | tcc | acg | tat | gag | ttc | cct | gaa | ggc | aga | gct | 432 |
| Tyr | Leu | Asp | Arg | Phe | Leu | Ser | Thr | Tyr | Glu | Phe | Pro | Glu | Gly | Arg | Ala | |
| | 130 | | | | | 135 | | | | | 140 | | | | | |

| tgg | atg | act | cag | ctc | ttg | gca | gtg | gct | tgc | ttg | tct | ttg | gct | tcg | aaa | 480 |
| Trp | Met | Thr | Gln | Leu | Leu | Ala | Val | Ala | Cys | Leu | Ser | Leu | Ala | Ser | Lys | |
| 145 | | | | 150 | | | | | 155 | | | | | 160 | | |

| atc | gaa | gag | act | ttt | gtg | cca | ctc | ccc | ttg | gat | ttg | cag | gta | gcg | gag | 528 |
| Ile | Glu | Glu | Thr | Phe | Val | Pro | Leu | Pro | Leu | Asp | Leu | Gln | Val | Ala | Glu | |
| | | | | 165 | | | | | 170 | | | | | 175 | | |

| gca | aag | ttt | gtt | ttt | gag | gga | agg | acc | ata | aaa | agg | atg | gag | ctt | ctg | 576 |
| Ala | Lys | Phe | Val | Phe | Glu | Gly | Arg | Thr | Ile | Lys | Arg | Met | Glu | Leu | Leu | |
| | | | 180 | | | | | 185 | | | | | 190 | | | |

| gtg | cta | agc | acc | tta | aag | tgg | agg | atg | cat | gct | gtt | act | gct | tgc | tca | 624 |
| Val | Leu | Ser | Thr | Leu | Lys | Trp | Arg | Met | His | Ala | Val | Thr | Ala | Cys | Ser | |
| | | 195 | | | | | 200 | | | | | 205 | | | | |

| ttt | gtt | gaa | tac | ttt | ctt | cat | aaa | ttg | agt | gat | cat | ggt | gca | ccc | tcc | 672 |

```
                Phe Val Glu Tyr Phe Leu His Lys Leu Ser Asp His Gly Ala Pro Ser
                    210                 215                 220 ttg ctt gca cgc tct cgc tct tcg gac ctt gtc ttg agc acc gct aaa          720
Leu Leu Ala Arg Ser Arg Ser Ser Asp Leu Val Leu Ser Thr Ala Lys
225                 230                 235                 240 ggt gct gaa ttc gtg gta ttc aga ccc tcc gag att gct gcc agt gtt          768
Gly Ala Glu Phe Val Val Phe Arg Pro Ser Glu Ile Ala Ala Ser Val
                245                 250                 255 gca ctt gct gct atc ggc gaa tgc agg agt tct gta att gag aga gct          816
Ala Leu Ala Ala Ile Gly Glu Cys Arg Ser Ser Val Ile Glu Arg Ala
            260                 265                 270 gct agt agc tgc aaa tat ttg gac aag gag agg gtt tta aga tgc cat          864
Ala Ser Ser Cys Lys Tyr Leu Asp Lys Glu Arg Val Leu Arg Cys His
        275                 280                 285 gaa atg att caa gag aag att act atg gga agc att gtc cta aag tct          912
Glu Met Ile Gln Glu Lys Ile Thr Met Gly Ser Ile Val Leu Lys Ser
    290                 295                 300 gct gga tca tca atc tcc tct gtg cca caa agc cca ata ggt gtc ctg          960
Ala Gly Ser Ser Ile Ser Ser Val Pro Gln Ser Pro Ile Gly Val Leu
305                 310                 315                 320 gac gct gca gcc tgt ctg agt caa caa agc gat gac gct act gtc ggg         1008
Asp Ala Ala Ala Cys Leu Ser Gln Gln Ser Asp Asp Ala Thr Val Gly
                325                 330                 335 tct cct gca gta tgt tac cat agt tct tcc aca agc aag agg aga atg         1056
Ser Pro Ala Val Cys Tyr His Ser Ser Ser Thr Ser Lys Arg Arg Met
            340                 345                 350 atc act aga cgt cta ctc taa                                             1077
Ile Thr Arg Arg Leu Leu *
        355

<210> SEQ ID NO 12
<211> LENGTH: 358
<212> TYPE: PRT
<213> ORGANISM: Zea mays

<400> SEQUENCE: 12

Met Val Pro Gly Tyr Asp Cys Ala Ala Ser Val Leu Leu Cys Ala Glu
1               5                   10                  15

Asp Asn Ala Ala Ile Leu Gly Leu Asp Asp Asp Gly Glu Glu Ser Ser
            20                  25                  30

Trp Ala Ala Ala Ala Thr Pro Pro Arg Asp Thr Val Ala Ala Ala Ala
        35                  40                  45

Ala Thr Gly Val Ala Val Asp Gly Ile Leu Thr Glu Phe Pro Leu Leu
    50                  55                  60

Ser Asp Asp Cys Val Ala Thr Leu Val Glu Lys Glu Val Glu His Met
65                  70                  75                  80

Pro Ala Glu Gly Tyr Leu Gln Lys Leu Gln Arg Arg His Gly Asp Leu
                85                  90                  95

Asp Leu Val Ala Val Arg Lys Asp Ala Ile Asp Trp Ile Trp Lys Val
            100                 105                 110

Ile Glu His Tyr Asn Phe Ala Pro Leu Thr Ala Val Leu Ser Val Asn
        115                 120                 125

Tyr Leu Asp Arg Phe Leu Ser Thr Tyr Glu Phe Pro Glu Gly Arg Ala
    130                 135                 140

Trp Met Thr Gln Leu Leu Ala Val Ala Cys Leu Ser Leu Ala Ser Lys
145                 150                 155                 160

Ile Glu Glu Thr Phe Val Pro Leu Pro Leu Asp Leu Gln Val Ala Glu
                165                 170                 175
```

```
Ala Lys Phe Val Phe Glu Gly Arg Thr Ile Lys Arg Met Glu Leu Leu
            180                 185                 190

Val Leu Ser Thr Leu Lys Trp Arg Met His Ala Val Thr Ala Cys Ser
        195                 200                 205

Phe Val Glu Tyr Phe Leu His Lys Leu Ser Asp His Gly Ala Pro Ser
    210                 215                 220

Leu Leu Ala Arg Ser Arg Ser Ser Asp Leu Val Leu Ser Thr Ala Lys
225                 230                 235                 240

Gly Ala Glu Phe Val Val Phe Arg Pro Ser Glu Ile Ala Ala Ser Val
                245                 250                 255

Ala Leu Ala Ala Ile Gly Glu Cys Arg Ser Ser Val Ile Glu Arg Ala
            260                 265                 270

Ala Ser Ser Cys Lys Tyr Leu Asp Lys Glu Arg Val Leu Arg Cys His
        275                 280                 285

Glu Met Ile Gln Glu Lys Ile Thr Met Gly Ser Ile Val Leu Lys Ser
    290                 295                 300

Ala Gly Ser Ser Ile Ser Ser Val Pro Gln Ser Pro Ile Gly Val Leu
305                 310                 315                 320

Asp Ala Ala Ala Cys Leu Ser Gln Gln Ser Asp Ala Thr Val Gly
                325                 330                 335

Ser Pro Ala Val Cys Tyr His Ser Ser Thr Ser Lys Arg Arg Met
            340                 345                 350

Ile Thr Arg Arg Leu Leu
        355

<210> SEQ ID NO 13
<211> LENGTH: 1173
<212> TYPE: DNA
<213> ORGANISM: Zea mays
<220> FEATURE:
<221> NAME/KEY: CDS
<222> LOCATION: (1)...(1173)

<400> SEQUENCE: 13 atg gcg ccg agc tgc tac gac gcg gca gcg tcc atg ctc ctc tgc gcc      48
Met Ala Pro Ser Cys Tyr Asp Ala Ala Ala Ser Met Leu Leu Cys Ala
 1               5                  10                  15 gag gag cac agc agc atc ctg tgg tac gac gag gag gag gag gag ctg      96
Glu Glu His Ser Ser Ile Leu Trp Tyr Asp Glu Glu Glu Glu Glu Leu
             20                  25                  30 gag gcg gtc ggg aga agg aga ggc cgg tcg ccg ggc tac ggg gac gac     144
Glu Ala Val Gly Arg Arg Arg Gly Arg Ser Pro Gly Tyr Gly Asp Asp
         35                  40                  45 ttc ggc gcg gac ttg ttc ccg ccg cag tcg gag gaa tgc gtg gcc ggt     192
Phe Gly Ala Asp Leu Phe Pro Pro Gln Ser Glu Glu Cys Val Ala Gly
     50                  55                  60 ctg gtg gag cgg gaa cgg gac cac atg ccg ggg ccg tgc tac ggc gac     240
Leu Val Glu Arg Glu Arg Asp His Met Pro Gly Pro Cys Tyr Gly Asp
 65                  70                  75                  80 agg ctg cgc ggc ggc ggc ggc tgt ctc tgc gtc cgc cgg gag gcc gtc     288
Arg Leu Arg Gly Gly Gly Gly Cys Leu Cys Val Arg Arg Glu Ala Val
                 85                  90                  95 gac tgg att tgg aag gct tac acg cac cac agg ttc cgc cct ctc act     336
Asp Trp Ile Trp Lys Ala Tyr Thr His His Arg Phe Arg Pro Leu Thr
            100                 105                 110 gcc tac ttg gca gtg aac tac ctc gat cgc ttc ctc tcg ctg tct gag     384
Ala Tyr Leu Ala Val Asn Tyr Leu Asp Arg Phe Leu Ser Leu Ser Glu
        115                 120                 125
```

```
gtg ccg gac ggc aag gac tgg atg acg cag ctc ctc gcg gtg gcg tgc      432
Val Pro Asp Gly Lys Asp Trp Met Thr Gln Leu Leu Ala Val Ala Cys
130                 135                 140 gtt tct ctg gcc gcc aag atg gag gaa acc gcc gtc ccg cag tgc ctg      480
Val Ser Leu Ala Ala Lys Met Glu Glu Thr Ala Val Pro Gln Cys Leu
145                 150                 155                 160 gac ctt cag gtc gga gac gcg cgg tac gtg ttc gag gcg aag acg gtc      528
Asp Leu Gln Val Gly Asp Ala Arg Tyr Val Phe Glu Ala Lys Thr Val
                165                 170                 175 cag agg atg gag ctc ctg gtt cta aca acc ctc aac tgg agg atg cat      576
Gln Arg Met Glu Leu Leu Val Leu Thr Thr Leu Asn Trp Arg Met His
    180                 185                 190 gcc gtg acg ccg ttc tcc tac gtg gat tac ttc ctg aac aag ctc agc      624
Ala Val Thr Pro Phe Ser Tyr Val Asp Tyr Phe Leu Asn Lys Leu Ser
        195                 200                 205 aac ggc ggc agc acg gcg ccg agg agc tgc tgg ctc ttg cag tcc gcg      672
Asn Gly Gly Ser Thr Ala Pro Arg Ser Cys Trp Leu Leu Gln Ser Ala
210                 215                 220 gag ctt atc ttg cgt gcg gcc aga gga acc ggc tgc gtc ggg ttc agg      720
Glu Leu Ile Leu Arg Ala Ala Arg Gly Thr Gly Cys Val Gly Phe Arg
225                 230                 235                 240 ccg tcc gag atc gcc gcc gcg gtt gca gcc gcc gtg gcc gga gac gtg      768
Pro Ser Glu Ile Ala Ala Ala Val Ala Ala Ala Val Ala Gly Asp Val
                245                 250                 255 gac gac gcg gac ggc gtc gag aac gcc tgc tgc gct cac gta gat aag      816
Asp Asp Ala Asp Gly Val Glu Asn Ala Cys Cys Ala His Val Asp Lys
                260                 265                 270 gag cgg gtg ttg cgg tgc cag gaa gcg atc ggg tcc atg gcg tcc tcg      864
Glu Arg Val Leu Arg Cys Gln Glu Ala Ile Gly Ser Met Ala Ser Ser
    275                 280                 285 gcg gcc att gac ggc gac gct acc gtg cca ccg aaa tct gcg aga cgc      912
Ala Ala Ile Asp Gly Asp Ala Thr Val Pro Pro Lys Ser Ala Arg Arg
290                 295                 300 agg agc tcc ccc gtg ccc gtg ccc gtg ccc gtg ccg cag agc cct gtg      960
Arg Ser Ser Pro Val Pro Val Pro Val Pro Val Pro Gln Ser Pro Val
305                 310                 315                 320 ggg gtg ctg gac gcg gcc gcc tgc ctc agc tac agg agc gaa gag gca     1008
Gly Val Leu Asp Ala Ala Ala Cys Leu Ser Tyr Arg Ser Glu Glu Ala
                325                 330                 335 gcg act gcg act gcg act tct gct gcc tca cat ggg ccc cct ggc tct     1056
Ala Thr Ala Thr Ala Thr Ser Ala Ala Ser His Gly Pro Pro Gly Ser
                340                 345                 350 tca agc tcg tcc tcg acc tcc ccg gtg acc agc aaa agg agg aaa ctc     1104
Ser Ser Ser Ser Ser Thr Ser Pro Val Thr Ser Lys Arg Arg Lys Leu
    355                 360                 365 gcc agc cga tgt gat gga tcg tgc agt gac cgg tca aag cgc gcg ccc     1152
Ala Ser Arg Cys Asp Gly Ser Cys Ser Asp Arg Ser Lys Arg Ala Pro
370                 375                 380 gcc caa tgg acc aaa gag tga                                          1173
Ala Gln Trp Thr Lys Glu *
385                 390

<210> SEQ ID NO 14
<211> LENGTH: 390
<212> TYPE: PRT
<213> ORGANISM: Zea mays

<400> SEQUENCE: 14

Met Ala Pro Ser Cys Tyr Asp Ala Ala Ala Ser Met Leu Leu Cys Ala
1               5                   10                  15
```

```
Glu Glu His Ser Ser Ile Leu Trp Tyr Asp Glu Glu Glu Glu Leu
                20                  25                  30

Glu Ala Val Gly Arg Arg Gly Arg Ser Pro Gly Tyr Gly Asp Asp
            35                  40                  45

Phe Gly Ala Asp Leu Phe Pro Pro Gln Ser Glu Glu Cys Val Ala Gly
 50                      55                  60

Leu Val Glu Arg Glu Arg Asp His Met Pro Gly Pro Cys Tyr Gly Asp
 65                  70                  75                  80

Arg Leu Arg Gly Gly Gly Cys Leu Cys Val Arg Arg Glu Ala Val
                85                  90                  95

Asp Trp Ile Trp Lys Ala Tyr Thr His His Arg Phe Arg Pro Leu Thr
                100                 105                 110

Ala Tyr Leu Ala Val Asn Tyr Leu Asp Arg Phe Leu Ser Leu Ser Glu
            115                 120                 125

Val Pro Asp Gly Lys Asp Trp Met Thr Gln Leu Leu Ala Val Ala Cys
            130                 135                 140

Val Ser Leu Ala Ala Lys Met Glu Glu Thr Ala Val Pro Gln Cys Leu
145                 150                 155                 160

Asp Leu Gln Val Gly Asp Ala Arg Tyr Val Phe Glu Ala Lys Thr Val
                165                 170                 175

Gln Arg Met Glu Leu Leu Val Leu Thr Thr Leu Asn Trp Arg Met His
            180                 185                 190

Ala Val Thr Pro Phe Ser Tyr Val Asp Tyr Phe Leu Asn Lys Leu Ser
            195                 200                 205

Asn Gly Gly Ser Thr Ala Pro Arg Ser Cys Trp Leu Leu Gln Ser Ala
            210                 215                 220

Glu Leu Ile Leu Arg Ala Ala Arg Gly Thr Gly Cys Val Gly Phe Arg
225                 230                 235                 240

Pro Ser Glu Ile Ala Ala Ala Val Ala Ala Ala Val Ala Gly Asp Val
                245                 250                 255

Asp Asp Ala Asp Gly Val Glu Asn Ala Cys Cys Ala His Val Asp Lys
            260                 265                 270

Glu Arg Val Leu Arg Cys Gln Glu Ala Ile Gly Ser Met Ala Ser Ser
            275                 280                 285

Ala Ala Ile Asp Gly Asp Ala Thr Val Pro Pro Lys Ser Ala Arg Arg
            290                 295                 300

Arg Ser Ser Pro Val Pro Val Pro Val Pro Gln Ser Pro Val
305                 310                 315                 320

Gly Val Leu Asp Ala Ala Ala Cys Leu Ser Tyr Arg Ser Glu Glu Ala
            325                 330                 335

Ala Thr Ala Thr Ala Thr Ser Ala Ala Ser His Gly Pro Pro Gly Ser
            340                 345                 350

Ser Ser Ser Ser Thr Ser Pro Val Thr Ser Lys Arg Arg Lys Leu
            355                 360                 365

Ala Ser Arg Cys Asp Gly Ser Cys Ser Asp Arg Ser Lys Arg Ala Pro
370                 375                 380

Ala Gln Trp Thr Lys Glu
385                 390

<210> SEQ ID NO 15
<211> LENGTH: 24
<212> TYPE: DNA
<213> ORGANISM: Zea mays
<220> FEATURE:
```

```
<221> NAME/KEY: primer_bind
<222> LOCATION: (1)...(24)

<400> SEQUENCE: 15
cacgcgcacc agcccaccgc ccag                                          24

<210> SEQ ID NO 16
<211> LENGTH: 25
<212> TYPE: DNA
<213> ORGANISM: Zea mays
<220> FEATURE:
<221> NAME/KEY: protein_bind
<222> LOCATION: (1)...(25)

<400> SEQUENCE: 16
tcccatcgga tctcctctag cgccc                                         25

<210> SEQ ID NO 17
<211> LENGTH: 21
<212> TYPE: DNA
<213> ORGANISM: Zea mays
<220> FEATURE:
<221> NAME/KEY: primer_bind
<222> LOCATION: (1)...(21)

<400> SEQUENCE: 17
tcactctttg gtccattggg c                                             21

<210> SEQ ID NO 18
<211> LENGTH: 24
<212> TYPE: DNA
<213> ORGANISM: Zea mays
<220> FEATURE:
<221> NAME/KEY: primer_bind
<222> LOCATION: (1)...(24)

<400> SEQUENCE: 18
tcaattcact cttggtccat tggg                                          24

<210> SEQ ID NO 19
<211> LENGTH: 25
<212> TYPE: DNA
<213> ORGANISM: Zea mays
<220> FEATURE:
<221> NAME/KEY: primer_bind
<222> LOCATION: (1)...(25)

<400> SEQUENCE: 19
tgcgccgagg agcacagcag catcc                                         25

<210> SEQ ID NO 20
<211> LENGTH: 25
<212> TYPE: DNA
<213> ORGANISM: Zea mays
<220> FEATURE:
<221> NAME/KEY: protein_bind
<222> LOCATION: (1)...(25)

<400> SEQUENCE: 20
gaccggtcac tgcacgatcc atcac                                         25

<210> SEQ ID NO 21
<211> LENGTH: 1734
<212> TYPE: DNA
<213> ORGANISM: Zea mays
<220> FEATURE:
<221> NAME/KEY: CDS
```

<222> LOCATION: (213)...(1262)

<400> SEQUENCE: 21

```
ccacgcgtcc ggggagggaa ttccttcctc cttttctgtt cggcgccgtg ctcgcgcgca      60
cccacccgca cgccccagta cccccacgct gcacagtgca cgccgacttt cctccgcctt     120
gctgctgcaa gtccgcaacc actggaggaa aaatctttc cttcactttt cttccctttc      180
cccccgcgca tgcacgggct ctgattgacg cc atg ggg gac gcc gcg gcc tcc       233
                                    Met Gly Asp Ala Ala Ala Ser
                                     1               5
```

| acg | tcc | gct | ccc | acc | acg | ccc | acc | tcc | atc | ctc | atc | tgc | ctg | gaa | gac |     281 |
|-----|-----|-----|-----|-----|-----|-----|-----|-----|-----|-----|-----|-----|-----|-----|-----|---------|
| Thr | Ser | Ala | Pro | Thr | Thr | Pro | Thr | Ser | Ile | Leu | Ile | Cys | Leu | Glu | Asp |         |
|     | 10  |     |     |     |     | 15  |     |     |     |     | 20  |     |     |     |     |         |

| ggc | agc | gac | ctt | ctc | gcc | gat | gcc | gac | gat | ggc | gcc | ggc | act | gac | ctc |     329 |
|-----|-----|-----|-----|-----|-----|-----|-----|-----|-----|-----|-----|-----|-----|-----|-----|---------|
| Gly | Ser | Asp | Leu | Leu | Ala | Asp | Ala | Asp | Asp | Gly | Ala | Gly | Thr | Asp | Leu |         |
|     | 25  |     |     |     | 30  |     |     |     |     | 35  |     |     |     |     |     |         |

| gtt | gtc | gcc | cgc | gac | gaa | cgt | ctg | ctt | gtc | gtg | gac | cag | gac | gag | gag |     377 |
|-----|-----|-----|-----|-----|-----|-----|-----|-----|-----|-----|-----|-----|-----|-----|-----|---------|
| Val | Val | Ala | Arg | Asp | Glu | Arg | Leu | Leu | Val | Val | Asp | Gln | Asp | Glu | Glu |         |
| 40  |     |     |     |     | 45  |     |     |     |     | 50  |     |     |     |     | 55  |         |

| tat | gta | gcg | ctg | ctc | ctg | tcc | aag | gag | agc | gcg | tca | ggc | ggc | ggc | ggc |     425 |
|-----|-----|-----|-----|-----|-----|-----|-----|-----|-----|-----|-----|-----|-----|-----|-----|---------|
| Tyr | Val | Ala | Leu | Leu | Leu | Ser | Lys | Glu | Ser | Ala | Ser | Gly | Gly | Gly | Gly |         |
|     |     |     | 60  |     |     |     |     | 65  |     |     |     |     | 70  |     |     |         |

| ccg | gtg | gag | gaa | atg | gag | gac | tgg | atg | aag | gcc | gcg | cgc | tcc | gga | tgc |     473 |
|-----|-----|-----|-----|-----|-----|-----|-----|-----|-----|-----|-----|-----|-----|-----|-----|---------|
| Pro | Val | Glu | Glu | Met | Glu | Asp | Trp | Met | Lys | Ala | Ala | Arg | Ser | Gly | Cys |         |
|     |     |     |     | 75  |     |     |     |     | 80  |     |     |     |     | 85  |     |         |

| gtc | cgc | tgg | atc | atc | aag | acc | acg | gcg | atg | ttc | cgg | ttc | ggc | ggg | aag |     521 |
|-----|-----|-----|-----|-----|-----|-----|-----|-----|-----|-----|-----|-----|-----|-----|-----|---------|
| Val | Arg | Trp | Ile | Ile | Lys | Thr | Thr | Ala | Met | Phe | Arg | Phe | Gly | Gly | Lys |         |
|     |     | 90  |     |     |     |     | 95  |     |     |     |     | 100 |     |     |     |         |

| acc | gct | tac | gtc | gcg | gtg | aat | tac | ctc | gat | cgc | ttc | ctg | gcg | caa | cgg |     569 |
|-----|-----|-----|-----|-----|-----|-----|-----|-----|-----|-----|-----|-----|-----|-----|-----|---------|
| Thr | Ala | Tyr | Val | Ala | Val | Asn | Tyr | Leu | Asp | Arg | Phe | Leu | Ala | Gln | Arg |         |
|     | 105 |     |     |     |     | 110 |     |     |     |     | 115 |     |     |     |     |         |

| cga | gtc | aat | agg | gag | cat | gcg | tgg | ggt | ctg | cag | ctg | ctc | atg | gtg | gcg |     617 |
|-----|-----|-----|-----|-----|-----|-----|-----|-----|-----|-----|-----|-----|-----|-----|-----|---------|
| Arg | Val | Asn | Arg | Glu | His | Ala | Trp | Gly | Leu | Gln | Leu | Leu | Met | Val | Ala |         |
| 120 |     |     |     |     | 125 |     |     |     |     | 130 |     |     |     |     | 135 |         |

| tgc | atg | tcg | ctg | gcg | acc | aag | ctg | gag | gag | cac | cac | gct | ccg | cgg | ctg |     665 |
|-----|-----|-----|-----|-----|-----|-----|-----|-----|-----|-----|-----|-----|-----|-----|-----|---------|
| Cys | Met | Ser | Leu | Ala | Thr | Lys | Leu | Glu | Glu | His | His | Ala | Pro | Arg | Leu |         |
|     |     |     | 140 |     |     |     |     | 145 |     |     |     |     | 150 |     |     |         |

| tcg | gag | ttg | ccc | ctg | gac | gcg | tgc | gag | ttc | gcg | ttc | gac | cgc | gcg | tcc |     713 |
|-----|-----|-----|-----|-----|-----|-----|-----|-----|-----|-----|-----|-----|-----|-----|-----|---------|
| Ser | Glu | Leu | Pro | Leu | Asp | Ala | Cys | Glu | Phe | Ala | Phe | Asp | Arg | Ala | Ser |         |
|     |     |     |     | 155 |     |     |     |     | 160 |     |     |     |     | 165 |     |         |

| gtg | ctg | cgg | atg | gag | ctc | ctc | gtc | ctg | ggc | acc | ctc | gag | tgg | cgg | atg |     761 |
|-----|-----|-----|-----|-----|-----|-----|-----|-----|-----|-----|-----|-----|-----|-----|-----|---------|
| Val | Leu | Arg | Met | Glu | Leu | Leu | Val | Leu | Gly | Thr | Leu | Glu | Trp | Arg | Met |         |
|     |     | 170 |     |     |     |     | 175 |     |     |     |     | 180 |     |     |     |         |

| gtc | gcc | gtc | acc | ccc | ttc | ccc | tac | atc | agc | tgc | ttc | gcg | gcg | cgg | ttc |     809 |
|-----|-----|-----|-----|-----|-----|-----|-----|-----|-----|-----|-----|-----|-----|-----|-----|---------|
| Val | Ala | Val | Thr | Pro | Phe | Pro | Tyr | Ile | Ser | Cys | Phe | Ala | Ala | Arg | Phe |         |
|     | 185 |     |     |     |     | 190 |     |     |     |     | 195 |     |     |     |     |         |

| cgg | cag | gac | gag | cgc | cgg | gcg | gtc | ctc | gtg | cgc | gcc | gtg | gag | tgc | gtc |     857 |
|-----|-----|-----|-----|-----|-----|-----|-----|-----|-----|-----|-----|-----|-----|-----|-----|---------|
| Arg | Gln | Asp | Glu | Arg | Arg | Ala | Val | Leu | Val | Arg | Ala | Val | Glu | Cys | Val |         |
| 200 |     |     |     |     | 205 |     |     |     |     | 210 |     |     |     |     | 215 |         |

| ttc | gcg | gcg | atc | aga | gcg | atg | agc | tcg | gtg | gag | tac | cag | ccg | tcg | acc |     905 |
|-----|-----|-----|-----|-----|-----|-----|-----|-----|-----|-----|-----|-----|-----|-----|-----|---------|
| Phe | Ala | Ala | Ile | Arg | Ala | Met | Ser | Ser | Val | Glu | Tyr | Gln | Pro | Ser | Thr |         |
|     |     |     | 220 |     |     |     |     | 225 |     |     |     |     | 230 |     |     |         |

| atc | gcc | gta | gca | tcc | atc | ctc | gtc | gct | cgc | ggc | agg | gag | acg | ccc | gcc |     953 |
|-----|-----|-----|-----|-----|-----|-----|-----|-----|-----|-----|-----|-----|-----|-----|-----|---------|
| Ile | Ala | Val | Ala | Ser | Ile | Leu | Val | Ala | Arg | Gly | Arg | Glu | Thr | Pro | Ala |         |
|     |     |     | 235 |     |     |     |     | 240 |     |     |     |     | 245 |     |     |         |

| ggc | aat | ctg | gac | gcg | ctc | aag | gcg | atc | ctg | ggc | tca | tca | ttt | ccg | cag |    1001 |
|-----|-----|-----|-----|-----|-----|-----|-----|-----|-----|-----|-----|-----|-----|-----|-----|---------|
| Gly | Asn | Leu | Asp | Ala | Leu | Lys | Ala | Ile | Leu | Gly | Ser | Ser | Phe | Pro | Gln |         |
|     |     |     | 250 |     |     |     |     | 255 |     |     |     |     | 260 |     |     |         |

| cta | gac | acc | ggg | cat | gtg | tac | tcc | tgc | tac | agc | gca | atg | att | cgg | gag |    1049 |

```
Leu Asp Thr Gly His Val Tyr Ser Cys Tyr Ser Ala Met Ile Arg Glu
        265                 270                 275 gac gac aag tcg ccg acg cag tcg acg tcg acg ggg gtg gcg             1097
Asp Asp Lys Ser Pro Thr Gln Ser Thr Ser Thr Gly Val Ala
280                 285                 290                 295 tcc tcg ggc gtc tct gtc gcc gcg cac gcc ggg ggg agc ggg agt ccc     1145
Ser Ser Gly Val Ser Val Ala Ala His Ala Gly Gly Ser Gly Ser Pro
                300                 305                 310 agc ccc ccg ggc gct tcc gtg tcc gtg ggc gcc aat aat gcc gct ggc     1193
Ser Pro Pro Gly Ala Ser Val Ser Val Gly Ala Asn Asn Ala Ala Gly
                315                 320                 325 acc gcc ccg ccg gca acc acg gac aac cgc aac aag agg aga cgg ttg     1241
Thr Ala Pro Pro Ala Thr Thr Asp Asn Arg Asn Lys Arg Arg Arg Leu
            330                 335                 340 cgc tca cct cag cga cag tag gagcagctca gctgctggca gtgcattgca        1292
Arg Ser Pro Gln Arg Gln  *
        345 gtgcagtgca gtccagctgc gttttctttt ttcagctcac catttccttt tgctgccgat   1352 tgtttcttca ggggtggccg tagagtgatt tggtaattta gtgccggaaa gattagtgcg   1412 gtgtcgcaga gtgatttggt aatttagtgc cggaaagatt tctttgtttt gaggagatct   1472 ttcgcgggac caaagggagg ggggcagtgt aaagacgaca gaacaagcgt gaaggcctcg   1532 agagtcgaga cctcacaggg taccgcctag cgcctactgg ggtgaaagtg aagtcaagga   1592 gtcgggaggg tgtgtgtgaa taccgtttgt agcagctagt gcgtccgtct gtcttttttt   1652 ttttctttct gttattaat tattaatagc ctgctagatt tcatttaaaa aaaaaaaaaa    1712 aaaaaaaaaa aaaaaaaaaa aa                                            1734

<210> SEQ ID NO 22
<211> LENGTH: 349
<212> TYPE: PRT
<213> ORGANISM: Zea mays

<400> SEQUENCE: 22

Met Gly Asp Ala Ala Ala Ser Thr Ser Ala Pro Thr Thr Pro Thr Ser
1               5                   10                  15

Ile Leu Ile Cys Leu Glu Asp Gly Ser Asp Leu Leu Ala Asp Ala Asp
            20                  25                  30

Asp Gly Ala Gly Thr Asp Leu Val Val Ala Arg Asp Glu Arg Leu Leu
        35                  40                  45

Val Val Asp Gln Asp Glu Glu Tyr Val Ala Leu Leu Leu Ser Lys Glu
    50                  55                  60

Ser Ala Ser Gly Gly Gly Gly Pro Val Glu Glu Met Glu Asp Trp Met
65                  70                  75                  80

Lys Ala Ala Arg Ser Gly Cys Val Arg Trp Ile Ile Lys Thr Thr Ala
                85                  90                  95

Met Phe Arg Phe Gly Gly Lys Thr Ala Tyr Val Ala Val Asn Tyr Leu
            100                 105                 110

Asp Arg Phe Leu Ala Gln Arg Val Asn Arg Glu His Ala Trp Gly
        115                 120                 125

Leu Gln Leu Leu Met Val Ala Cys Met Ser Leu Ala Thr Lys Leu Glu
    130                 135                 140

Glu His His Ala Pro Arg Leu Ser Glu Leu Pro Leu Asp Ala Cys Glu
145                 150                 155                 160

Phe Ala Phe Asp Arg Ala Ser Val Leu Arg Met Glu Leu Leu Val Leu
                165                 170                 175
```

-continued

```
Gly Thr Leu Glu Trp Arg Met Val Ala Val Thr Pro Phe Pro Tyr Ile
            180                 185                 190

Ser Cys Phe Ala Ala Arg Phe Arg Gln Asp Glu Arg Arg Ala Val Leu
            195                 200                 205

Val Arg Ala Val Glu Cys Val Phe Ala Ala Ile Arg Ala Met Ser Ser
210                 215                 220

Val Glu Tyr Gln Pro Ser Thr Ile Ala Val Ala Ser Ile Leu Val Ala
225                 230                 235                 240

Arg Gly Arg Glu Thr Pro Ala Gly Asn Leu Asp Ala Leu Lys Ala Ile
            245                 250                 255

Leu Gly Ser Ser Phe Pro Gln Leu Asp Thr Gly His Val Tyr Ser Cys
            260                 265                 270

Tyr Ser Ala Met Ile Arg Glu Asp Asp Lys Ser Pro Thr Gln Ser Thr
            275                 280                 285

Ser Thr Ser Thr Gly Val Ala Ser Ser Gly Val Ser Val Ala Ala His
            290                 295                 300

Ala Gly Gly Ser Gly Ser Pro Ser Pro Pro Gly Ala Ser Val Ser Val
305                 310                 315                 320

Gly Ala Asn Asn Ala Ala Gly Thr Ala Pro Pro Ala Thr Thr Asp Asn
            325                 330                 335

Arg Asn Lys Arg Arg Arg Leu Arg Ser Pro Gln Arg Gln
            340                 345

<210> SEQ ID NO 23
<211> LENGTH: 21
<212> TYPE: DNA
<213> ORGANISM: Zea mays
<220> FEATURE:
<221> NAME/KEY: primer_bind
<222> LOCATION: (1)...(21)

<400> SEQUENCE: 23
cagtaccccc acgctgcaca g                                              21

<210> SEQ ID NO 24
<211> LENGTH: 26
<212> TYPE: DNA
<213> ORGANISM: Zea mays
<220> FEATURE:
<221> NAME/KEY: primer_bind
<222> LOCATION: (1)...(26)

<400> SEQUENCE: 24
tcacgcttgt tctgtcgtct ttacac                                         26

<210> SEQ ID NO 25
<211> LENGTH: 24
<212> TYPE: DNA
<213> ORGANISM: Zea mays
<220> FEATURE:
<221> NAME/KEY: primer_bind
<222> LOCATION: (1)...(24)

<400> SEQUENCE: 25
gctgctgcaa gtccgcaacc actg                                           24

<210> SEQ ID NO 26
<211> LENGTH: 25
<212> TYPE: DNA
<213> ORGANISM: Zea mays
<220> FEATURE:
```

-continued

```
<221> NAME/KEY: primer_bind
<222> LOCATION: (1)...(25)

<400> SEQUENCE: 26
cgcttgttct gtcgtcttta cactg                                              25

<210> SEQ ID NO 27
<211> LENGTH: 27
<212> TYPE: DNA
<213> ORGANISM: Zea mays
<220> FEATURE:
<221> NAME/KEY: primer_bind
<222> LOCATION: (1)...(27)

<400> SEQUENCE: 27
acctccatcc tcatctgcct ggaagac                                            27

<210> SEQ ID NO 28
<211> LENGTH: 24
<212> TYPE: DNA
<213> ORGANISM: Zea mays
<220> FEATURE:
<221> NAME/KEY: primer_bind
<222> LOCATION: (1)...(24)

<400> SEQUENCE: 28
ctggactgca ctgcactgca atgc                                               24

<210> SEQ ID NO 29
<211> LENGTH: 25
<212> TYPE: DNA
<213> ORGANISM: Zea mays
<220> FEATURE:
<221> NAME/KEY: primer_bind
<222> LOCATION: (1)...(25)

<400> SEQUENCE: 29
catcctcatc tgcctggaag acggc                                              25

<210> SEQ ID NO 30
<211> LENGTH: 23
<212> TYPE: DNA
<213> ORGANISM: Zea mays
<220> FEATURE:
<221> NAME/KEY: primer_bind
<222> LOCATION: (1)...(23)

<400> SEQUENCE: 30
aatgcactgc cagcagctga gct                                                23
```

CYCLIN D POLYNUCLEOTIDES, POLYPEPTIDES AND USES THEREOF

CROSS REFERENCE TO RELATED APPLICATIONS

This application claims priority to U.S. Patent Application No. 60/101,551, filed Sep. 23, 1998, to U.S. patent application Ser. No. 09/398,858, filed Sep. 20, 1999, now U.S. Pat. No. 6,518,487, and to U.S. patent application Ser. No. 10/320,230, filed Dec. 16, 2002, now abandoned, and to U.S. patent application Ser. No. 10/348,110, filed Jan. 21, 2003, now abandoned, all of which are incorporated by reference herewithin in their entirety.

TECHNICAL FIELD

The present invention relates generally to plant molecular biology. More specifically, it relates to nucleic acids and methods for modulating their expression in plants.

BACKGROUND OF THE INVENTION

Cell division plays a crucial role during all phases of plant development. The continuation of organogenesis and growth responses to a changing environment requires precise spatial, temporal and developmental regulation of cell division activity in meristems (and in cells with the capability to form new meristems such as in lateral root formation). Such control of cell division is also important in organs themselves (i.e. separate from meristems per se), for example, in leaf expansion, secondary growth, and endoreduplication.

A complex network controls cell proliferation in eukaryotes. Regulatory pathways communicate environmental constraints, such as nutrient availability, mitogenic signals such as growth factors or hormones, or developmental cues such as the transition from vegetative to reproductive. Ultimately, these regulatory pathways control the timing, frequency (rate), plane and position of cell divisions.

The basic mechanism of cell cycle control is conserved among eukaryotes. A catalytic protein serine/threonine kinase and an activating cyclin subunit control progress through the cell cycle. The protein kinase is generally referred to as a cyclin-dependent-kinase (CDK), whose activity is modulated by phosphorylation and dephosphorylation events and by their association with regulatory subunits called cyclins. CDKs require association with cyclins for activation, and the timing of activation is largely dependent upon cyclin expression. CDKs are a family of serine/threonine protein kinases that regulate individual cell cycle transitions.

Eukaryote genomes typically encode multiple cyclin and CDK genes. In higher eukaryotes, different members of the CDK family act in different stages of the cell cycle. Cyclin genes are classified according to the timing of their appearance during the cell cycle. In addition to cyclin and CDK subunits, CDKs are often physically associated with other proteins that alter localization, substrate specificity, or activity. A few examples of such CDK interacting proteins are the CDK inhibitors, members of the Retinoblastoma-associated protein (Rb) family, and the Constitutive Kinase Subunit (CKS).

The protein kinase activity of the complex is regulated by feedback control at certain checkpoints. At such checkpoints the CDK activity becomes limiting for further progress. When the feedback control network senses the completion of a checkpoint, CDK is activated and the cell passes through to the next checkpoint. Changes in CDK activity are regulated at multiple levels, including reversible phosphorylation of the cell cycle factors, changes in subcellular localization of the complex, and the rates of synthesis and destruction of limiting components. P. W. Doerner, Cell Cycle Regulation in Plants, *Plant Physiol.* (1994) 106:823-827.

Plants have unique developmental features that distinguish them from other eukaryotes. Plant cells do not migrate, and thus only cell division, expansion and programmed cell death determine morphogenesis. Organs are formed throughout the entire life span of the plant from specialized regions called meristems. In addition, many differentiated cells have the potential to both dedifferentiate and to reenter the cell cycle. There are also numerous examples of plant cell types that undergo endoreduplication, a process involving nuclear multiplication without cytokinesis. The study of plant cell cycle control genes is expected to contribute to the understanding of these unique phenomena. O, Shaul et al., Regulation of Cell Division in *Arabidopsis, Critical Reviews in Plant Sciences,* 15(2):97-112 (1996).

There is evidence to suggest that cells must be dividing for transformation to occur. It has also been observed that dividing cells represent only a fraction of cells that transiently express a transgene. Furthermore, the presence of damaged DNA in non-plant systems (similar to DNA introduced by particle gun or other physical means) has been well documented to rapidly induce cell cycle arrest (W. Siede, Cell cycle arrest in response to DNA damage: lessons from yeast, *Mutation Res.* 337(2):73-84). Therefore, to optimize transformation it would be desirable to provide a method for increasing the number of cells undergoing division.

Cell division in higher eukaryotes is controlled by two main checkpoints in the cell cycle that prevent the cell from entering either M- or S-phase of the cycle prematurely. Evidence from yeast and mammalian systems has repeatedly shown that over-expression of key cell cycle activating genes can either trigger cell division in non-dividing cells, or stimulate division in previously dividing cells (i.e. the duration of the cell cycle is decreased and cell size is reduced). Examples of genes whose over-expression has been shown to stimulate cell division include cyclins (see, e.g. Doerner, P. et al., *Nature* (1996) 380:520-423; Wang, T. C., et al., *Nature* (1994) 369:669-671; Quelle D. E., et al., *Genes Dev.* (1993) 7:1559-1571, E2F transcription factors (see, e.g. Johnson D. G. et al., *Nature* (1993) 365:349-352; Lukas, J. et al., (1996) *Mol. Cell. Biol.* 16:1047-1057), cdc25 (see, e.g. Bell, M. H. et al., (1993) *Plant Molecular Biology* 23:445-451; Draetta, D. et al., (1996) *BBA* 1332:53-63), and mdm2 (see, e.g. Teoh, G. et al., (1997) *Blood* 90:1982-1992). Conversely, other gene products have been found to participate in negative regulation and/or checkpoint control, effectively blocking or retarding progression through the cell cycle. (See MacLachlan, T. K. et al., (1995) *Critical Rev. Eukaroytic Gene Expression* 5(2): 127-156).

Current methods for genetic engineering in maize require a specific cell type as the recipient of new DNA. These cells are found in relatively undifferentiated, rapidly growing callus cells or on the scutellar surface of the immature embryo (which gives rise to callus). Irrespective of the delivery method currently used, DNA is introduced into literally thousands of cells, yet transformants are recovered at frequencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. (Bowen et al., Tucson International Mol. Biol. Meetings).

Over the period between 1950 and 1980, the increase in maize production worldwide outpaced both wheat and rice. Despite a temporary downswing in the early to mid-1980's (due to both environmental and political factors) world maize production has risen steadily from around 145 million tons in 1950 to nearly 500 million tons by 1990. Increases in yield and harvested area have been the predominant contributors to enhanced world production; with yield playing the major role in industrialized countries and area expansion being most important in developing countries. Yet, over the next ten years it's also predicted that meeting the demand for corn worldwide will require an additional 20% over current production (Dowswell, C. R., Paliwal, R. L., Cantrell, R. P. (1996) *Maize in the Third World*, Westview Press, Boulder, Colo.).

The components most often associated with maize productivity are grain yield or whole-plant harvest for animal feed (in the forms of silage, fodder, or stover). Thus the relative growth of the vegetative or reproductive organs might be preferred, depending on the ultimate use of the crop. Whether the whole plant or the ear are harvested, overall yield will depend strongly on vigor and growth rate. In modern maize hybrids, the impact of heterosis on overall plant vigor and yield has been unarguably demonstrated (Duvick, D. N. (1984) In: Genetic contributions to yield gains in five major crop plants. W. R. Fehr, ed. CSSA, Madison, Wis.). Corn breeders since the 1930's have been selectively breeding by identifying inbreds that in combination produce hybrid vigor well beyond either parent. Surprisingly little is known about why hybrids are so much larger than their parent inbreds, although there are some interesting observations in the literature. In metabolic studies, heterosis (increases over either parent) has been observed for physiological traits such as P uptake by roots (Baliger and Barber, 1979; Nielsen and Barber, 1978), but for many enzymatic traits the hybrid is often intermediate to the inbred parents (Hageman, R. H., Leng, E. R., Dudley, J. W. (1967) *Adv. Agron.* 19:45-86; Chevalier, P., Schrader, L. E. (1977) Crop Sci. 17:897-901; Schrader, L. E. (1974) *Crop Sci.* 14:201-205; Schrader, L. E. (1985) pp 79-89. In: Exploitation of physiological and genetic variability to enhance crop productivity. Harper, J. E. ed. *Am. Soc. Plant Physiol.* Rockville, Md., Schrader, L. E., Cataldo, D. A., Peterson, D. M., Vogelzang, R. D. (1974) *Plant Physiol.* 32:337-341).

Anatomical data is less confusing. In summarizing data from an earlier publication, Kiesselbach states that approximately 10% of the increased vigor of the hybrid over its inbred parents is due to cell enlargement, and 90% can be accounted for simply by increased cell numbers (Kiesselbach, T. A. 1922, 1949. The Structure and Reproduction of Corn, Nebraska Agric. Exp. Stn. Res. Bull. 161). This evidence for enhanced cell divisions contributing to increased maize vigor remains unchallenged. Recently it was shown that overexpressing a B cyclin in *Arabidopsis* resulted in increased root biomass and the root cells were smaller (indicative of accelerated cell division), but the overall plant morphology was not perturbed (Doerner et al., 1996). Similarly, expression of maize CycD genes in corn will enhance growth and biomass accumulation.

Other more specialized applications exist for these genes at the whole plant level. It has been demonstrated that endoreduplication occurs in numerous cell types within plants, but this is particularly prevalent in maize endosperm, the primary seed storage tissue. Under the direction of endosperm-specific promoters, expression of CycD genes (and possibly expression of CycD in conjunction with genes that inhibit mitosis) will further stimulate the process of endoreduplication.

SUMMARY OF THE INVENTION

Generally, it is the object of the present invention to provide nucleic acids and proteins relating to the control of cell division.

It is another object of the present invention to provide nucleic acids and proteins that can be used to identify other interacting proteins involved in cell cycle regulation.

It is another object of the present invention to provide antigenic fragments of the proteins of the present invention.

It is another object of the present invention to provide transgenic plants comprising the nucleic acids of the present invention.

It is another object of the present invention to provide methods for modulating, in a transgenic plant, the expression of the nucleic acids of the present invention.

It is another object of the present invention to provide a method for increasing the number of cells undergoing cell division.

It is another object of the present invention to provide a method for increasing crop yield.

It is another object of the present invention to provide a method for improving transformation frequencies.

It is another object of the present invention to provide a method for providing a positive growth advantage in a plant comprising modulating CycD protein expression.

It is another object of the present invention to provide a method for modulating cell growth.

It is another object of the present invention to provide a method for modulating cell division.

It is another object of the present invention to provide a method for modulating plant height or size.

It is another object of the present invention to provide a method for providing a positive growth advantage.

It is another object of the present invention to provide a method for increasing the growth rate.

It is another object of the present invention to provide a method for enhancing or inhibiting organ growth, for example seed, root, shoot, ear, tassel, stalk, pollen, stamen.

It is another object of the present invention to provide a method for producing organ ablation.

It is another object of the present invention to provide a method for producing parthenocarpic fruits.

It is another object of the present invention to provide a method for producing male sterile plants.

It is another object of the present invention to provide a method for enhancing embryogenic response, i.e. size or growth rate.

It is another object of the present invention to provide a method for increasing callus induction.

It is another object of the present invention to provide a method for positive selection.

It is another object of the present invention to provide a method for increasing plant regeneration.

It is another object of the present invention to provide a method for altering the percent of time that cells are arrested, i.e. in G1 or G0 stages of the cell cycle.

It is another object of the present invention to provide a method for altering the amount of time a cell spends in a particular cell cycle.

It is another object of the present invention to provide a method for improving in cells the response to environmental stress such as drought, heat, or cold.

It is another object of the present invention to provide a method for increasing the number of pods per plant.

It is another object of the present invention to provide a method for increasing the number of seeds per pod or ear.

It is another object of the present invention to provide a method for altering the lag time in seed development.

It is another object of the present invention to provide a method for providing hormone independent cell growth.

It is another object of the present invention to provide a method for increasing growth rate of cells in bioreactors.

Therefore, in one aspect, the present invention relates to an isolated nucleic acid comprising a member selected from the group consisting of:

(a) a polynucleotide that encodes a polypeptide of SEQ ID NOS: 2, 12, 14, or 22;

(b) a polynucleotide amplified from a monocot nucleic acid library using the primers of SEQ ID NOS: 3-10, 15-20 or 23-30;

(c) a polynucleotide having 20 contiguous bases of SEQ ID NOS: 1, 11, 13, or 21;

(d) a polynucleotide encoding a monocot cyclin D protein;

(e) a polynucleotide having at least 70% identity to the entire coding region of SEQ ID NOS: 1, 11, 13, or 21, wherein the % identity is determined by GCG/bestfit program using a gap creation penalty of 50 and a gap extension penalty of 3;

(f) a polynucleotide that hybridizes under stringent conditions to a nucleic acid characterized by SEQ ID NOS: 1, 11, 13, or 21, wherein the conditions include a wash in 0.1×SSC at 60 to 65° C.;

(g) a polynucleotide characterized by the sequences set forth in SEQ ID NOS: 1, 11, 13, or 21;

(h) An isolated nucleic acid amplified from a Zea mays nucleic acid library using the primers of SEQ ID NOS: 3-10, 15-20 or 23-30;

(i) a polynucleotide complementary to a polynucleotide of (a) through (g); and (j) a polynucleotide having the sequence of ATCC deposit having the Designation No. 98847 or 98848.

In another aspect, the present invention relates to recombinant expression cassettes, comprising the nucleic acid operably linked to a promoter.

In some embodiments, the nucleic acid is operably linked in antisense orientation to the promoter.

In another aspect, the present invention is directed to a host cell transfected with the recombinant expression cassette as described, supra.

In a further aspect, the present invention relates to an isolated protein comprising a polypeptide of at least 10 contiguous amino acids encoded by the isolated nucleic acid. In some embodiments, the polypeptide has a sequence selected from the group consisting of SEQ ID NOS: 2, 12, 14, and 22.

In another aspect, the present invention relates to an isolated nucleic acid comprising a polynucleotide of at least 25 nucleotides in length which selectively hybridizes under stringent conditions to a nucleic acid selected from the group consisting of SEQ ID NOS: 1, 11, 13, and 21, or a complement thereof. In some embodiments, the isolated nucleic acid is operably linked to a promoter.

In yet another aspect, the present invention relates to an isolated nucleic acid comprising a polynucleotide, the polynucleotide having at least 80% sequence identity to an identical length of a nucleic acid selected from the group consisting of SEQ ID NOS: 1, 11, 13, and 21 or a complement thereof.

In another aspect, the present invention relates to an isolated nucleic acid comprising a polynucleotide having a sequence of a nucleic acid amplified from a Zea mays nucleic acid library using the primers selected from the group consisting of SEQ ID NOS: 3-10, 15-20, and 23-30 or complements thereof. In some embodiments, the nucleic acid library is a cDNA library.

In another aspect, the present invention relates to a recombinant expression cassette comprising a nucleic acid amplified from a library as referred to supra, wherein the nucleic acid is operably linked to a promoter.

In some embodiments, the present invention relates to a host cell transfected with this recombinant expression cassette.

In some embodiments, the present invention relates to a protein of the present invention that is produced from this host cell.

In an additional aspect, the present invention is directed to an isolated nucleic acid comprising a polynucleotide encoding a polypeptide wherein: (a) the polypeptide comprises at least 10 contiguous amino acid residues from a first polypeptide selected from the group consisting of SEQ ID NOS: 2, 12, 14, and 22; (b) the polypeptide does not bind to antisera raised against the first polypeptide which has been fully immunosorbed with the first polypeptide; and (c) the polypeptide has a molecular weight in non-glycosylated form within 10% of the first polypeptide.

In a further aspect, the present invention relates to a heterologous promoter operably linked to a non-isolated polynucleotide of the present invention, wherein the polypeptide is encoded by a nucleic acid amplified from a nucleic acid library.

In yet another aspect, the present invention relates to a transgenic plant comprising a recombinant expression cassette comprising a plant promoter operably linked to any of the isolated nucleic acids of the present invention. The present invention also provides transgenic seed from the transgenic plant.

In a further aspect, the present invention relates to a method of modulating expression of the genes encoding the proteins of the present invention in a plant, comprising the steps of (a) transforming a plant cell with a recombinant expression cassette comprising a polynucleotide of the present invention operably linked to a promoter; (b) growing the plant cell under plant growing conditions; and (c) inducing expression of the polynucleotide for a time sufficient to modulate expression of the genes in the plant. Expression of the genes encoding the proteins of the present invention can be increased or decreased relative to a non-transformed control plant.

In another aspect of the invention an isolated protein is provided comprising a member selected from the group consisting of:

(a) a polypeptide comprising at least 25 contiguous amino acids of SEQ ID NOS: 2, 12, 14, or 22;

(b) a polypeptide which is a monocot cyclin D protein;

(c) a polypeptide comprising at least 65% sequence identity to SEQ ID NOS: 2, 12, 14, or 22, wherein the % sequence identity is based on the entire sequence and is determined by GAP 10 using default parameters;

(d) a polypeptide encoded by a nucleic acid of claim 1; and (e) a polypeptide characterized by SEQ ID NO: 2, 12, 14, or 22.

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof, which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246:1275-1281 (1989); and Ward, et al., *Nature* 341:544-546 (1989); and Vaughan et al., *Nature Biotech.* 14:309-314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome that can be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, U.S.A. 82:2306-2309 (1985)), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., *Nucl. Acids Res.* 17:477-498 (1989)). Thus, the maize preferred codon for a particular amino acid can be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control that is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell that contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA that has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids that are "isolated" as defined herein, are also referred to as "heterologous" nucleic acids.

Unless otherwise stated, the term "cell cycle nucleic acid" means a nucleic acid comprising a polynucleotide ("cell cycle polynucleotide") encoding a cell cycle polypeptide. A "cell cycle gene" refers to a non-heterologous genomic form of a full-length cell cycle polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules that comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds. *Current Protocols*, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof, that have the essential nature of a natural ribonucleotide in that they hybridize to nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties*, 2nd ed., T. E. Creighton, W. H. Freeman and Company, New York (1993). Many detailed reviews are available on this subject, such as, for example, those provided by Wold, F., *Posttranslational Protein Modifications: Perspectives and Prospects*, pp. 1-12 in *Posttranslational Covalent Modification of Proteins*, B. C. Johnson, Ed., Academic Press, New York (1983); Seifter et al., *Meth. Enzymol.* 182: 626-646 (1990) and Rattan et al., Protein Synthesis: Posttranslational Modifications and Aging, Ann. N.Y. *Acad. Sci.* 663:48-62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, seeds, fibers, xylem vessels, tracheids, or sclerenchyma. Such promoters are referred to as "tissue preferred". Promoters that initiate transcription only in certain tissue are referred to as "tissue specific". A "cell type" specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter that is active under most environmental conditions.

The term "cell cycle polypeptide" refers to one or more amino acid sequences, in glycosylated or non-glycosylated form, involved in the regulation of cell division. The term is also inclusive of fragments, variants, homologs, alleles or precursors (e.g., preproproteins or proproteins) thereof. A "cell cycle protein" comprises a cell cycle polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

Specific binding to an antibody under such conditions may require an antibody that is selected for its specificity for a particular protein. For example, antibodies raised to the polypeptides of the present invention can be selected from those antibodies that are specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Generally hybridization is conducted for a time in the range of from four to sixteen hours.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 *"Overview of principles of hybridization and the strategy of nucleic acid probe assays"*, Elsevier, N.Y. (1993); and *Current Protocols in Molecular Biology*, Chapter 2, Ausubel, et al., Eds., Greene Publishing and Wiley-Interscience, New York (1995).

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, Proc. *Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., Eds., Greene Publishing and Wiley-Interscience, New York (1995).

As those of ordinary skill in the art will understand, BLAST searches assume that proteins can be modeled as random sequences. However, many real proteins comprise regions of nonrandom sequences that may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.* 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. For purposes of defining the invention, % identity on the nucleic acid level is determined by the BESTFIT DNA Sequence Alignment software on Genescape using a gap weight of 50 and a length weight of 3. For purposes of defining the invention, % identity on the amino acid level is determined by the BESTFIT DNA Sequence Alignment software on Genescape using a gap weight of 12 and a length weight of 4.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 85%, more preferably at least 90%, and most preferably at least 98%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optimal alignment can be conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

By "two-hybrid system" is meant a screening method to identify protein-protein interactions, using a known gene (and its encoded product) as a "bait" or target and screening a library of expressed genes and their corresponding encoded products for specific interactions with the "bait" molecule. Methods for library construction and use of visual marker genes for yeast two-hybrid screens are well known in the art, and can be found in Sambrook, et al., 1990, Ausubel et al., 1990 and G. Hannon and P. Bartel, Identification of interacting proteins using the two-hybrid system. *Methods Mol. Cellular Biol.* 5:289-297 (1995).

DETAILED DESCRIPTION OF THE INVENTION

The CycD genes in plants encode proteins ranging from 37 to 44 kD. This protein is necessary for progression from G1 into S-phase. The encoded protein binds to CDK4, and this active cyclin D-CDK4 kinase hyperphosphorylates Rb, releasing the E2F transcription factor which activates DNA synthesis. G1/S phase cyclins were first isolated in yeast (Hadwiger et al., 1989; Richardson et al., 1989), and a few years later in humans (Matsushime et al., 1991). Subsequently, it has been cloned in various other organisms including plants. Three CycD isoforms have been found in both animals and plants, which are analogous to, and can complement function of, the three CLN genes originally identified in yeast. In mammalian cells, cyclins appear to be important integrators of growth signals for cell cycle control. In plants, this aspect has been best characterized in *Arabidopsis*, with AtCycD2 and AtCycD3 expression being induced by sucrose and cytokinin, respectively (Francis et al., 1998). AtCycD3 can also been induced by nitrate levels (Fuerst et al., 1998). CycD1 has been cloned in *Arabidopsis thaliana* (Soni et al., 1995; EMBL accession number X83369), *Antirrhinum majus* and *Helianthus tuberosum*. Cyclin D2 has been cloned in *Arabidopsis* (Soni et al, 1995; X83370), and CycD3 has been cloned in *Arabidopsis* (Soni et al., 1995; X83371), Antirrhinum, *Helianthus* (Freeman and Muray, unpublished), *Nicotiana* and *Medicago* (Dahl et al., 1995; X88864). No monocot homologs have been reported. In the present invention, we describe the full length clone of the maize CycD gene (designated ZmCycD).

In addition to the positive influence of transient cell cycle stimulation, stable expression of positive cell cycle regulators would be a benefit for positive selection schemes in the recovery of transgenic plants and plant cells. In a population of cells and/or callus growing in vitro, cells expressing a gene such as CycD will have a differential growth advantage based simply on their accelerated division rate. It would be expected that these transgenic cells or cell/clusters would grow more rapidly than their non-transformed counterparts in culture, permitting ready identification of transformants. Such a positive growth advantage (imparted by expression of a gene such as CycD, or CycD plus another cell cycle component), would also be beneficial in other types of transformation strategies, including as examples, protoplast transformation, leaf base transformation and transformation of cells in meristems. Such growth stimulation may also extend transformation protocols to tissues normally no amenable to culture. Examples would include such tissues as portions of leaves (in which the cells do not normally divide), scutellum from recalcitrant inbreds (in which cells typically are not induced to divide in culture), and nodal tissues, etc.

Of particular interest is the use of cell cycle genes such as CycD to impart a positive growth advantage to cells in the meristem, including apical initials. The apical initials in angiosperm shoot meristems are defined by their position within the meristem. If an apical initial cell becomes compromised relative to neighboring cells in the meristem, it will be replaced by an adjacent neighbor that is not at a disadvantage. This new cell assumes the role of the apical initial. Conversely, transgenic cells adjacent to the apical initials with a positive growth advantage can, over time (i.e. through successive cell generations), out-compete the wild-type apical initials, eventually replacing these cells and establishing a homogeneous transformed meristem.

There can also be organ and/or whole plant impacts to such cell cycle transgene expression.

REFERENCES

Renaudin, J-P., Doonan, J. H., Freeman, D., Hashimoto, J., Hirt, H., Inze, D., Jacobs, T., Kouchi, H., Rouze, P., Sauter, M., Savoure, A., Sorrell, D. A., Sundaresan, V., and Murray, J. A. H. 1996. Plant cyclins: a unified nomenclature for plant A-, B- and D-type cyclins based on sequence organization. Plant Molecular Biology 32:1003-1018.

Dahl, M., Meskiene, I., Boegre, L., Ha, D. T. C., Swoboda, I., Hubmann, R., Hirt, H. and Heberle-Bors, E. 1995. The D-type alfalfa cyclin gene cycMs4 complements G 1 cyclin-deficient yeast and is induced in the G-1 phase of the cell cycle. Plant Cell 7(11):1847-1857.

Murray, J. A. H., Freeman, D., Greenwood, J., Huntley, R., Makkerk, J. Riou-Khamlichi, C., Sorrell, D. A., Cockcroft, C., Carmichael., J. P., Soni, R. and Shah, Z. H. 1998. Plant D cyclins and retinoblastoma protein homologues. In: *Plant Cell Division*, (Francis, D., Dudits, D. and Inze D., eds.), Portland Press, London.

Fuerst, R. A. U. A., Soni, R., Murray, J. A. H. and Lindsey, K. 1998. Modulation of cyclin transcript levels in cultured cells of *Arabidopsis thaliana. Plant Physiol.* 112: 1023-1033.

Hadwiger, J. A., Wittenberg, C., Richardson, H. E., de Barros Lopes, M. and Reed, S. I. 1989. A family of cyclin homologs that control the G1 phase in yeast. *Proc. Natl. Acad. Sci. USA* 86(16):6255-6259.

Matsushime, H., Roussel, M. F. and Sherr, C. J. 1991. Novel mammalian cyclins (CYL genes) expressed during G1. Cold Spring Harb. *Symp. Quant Biol.* 56:69-74.

Richardson, H. E., Wittenberg, C., Cross, F and Reed, S. I. 1989. An essential G1 function for cyclin-like proteins in yeast. *Cell* 59(6):1127-1133.

Soni, R., Carmichael, J. P., shah, Z. H. and Murray, J. A. H. 1995. A family of cyclin D homologs from plants differentially controlled by growth regulators and containing the conserved retinoblastoma protein interaction motif. *Plant Cell* 7:85-103.

The present invention provides, inter alia, compositions and methods for modulating (i.e., increasing or decreasing) the total levels of proteins of the present invention and/or altering their ratios in plants. Thus, the present invention provides utility in such exemplary applications as the regulation of cell division. The polypeptides of the present invention can be expressed at times or in quantities that are not characteristic of non-recombinant plants.

In particular, modulating cell cycle proteins is expected to provide a positive growth advantage and increase crop yield. Cell cycle nucleic acids can be adducted to a second nucleic acid sequence encoding a DNA-binding domain, for use in two-hybrid systems to identify CycD-interacting proteins. It is expected that modulating the level of cell cycle protein, i.e. over-expression, will increase endoreduplication which is expected to increase the size of the seed, the size of the endosperm and amount of protein in the seed. The cell cycle protein can be used to affinity purify active maturation promoting factor (MPF) or its components.

The present invention also provides isolated nucleic acid comprising polynucleotides of sufficient length and complementarity to a cell cycle gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of cell cycle polypeptides, or for use as immunogens in the preparation and/or screening of antibodies. The isolated nucleic acids of the present invention can also be employed for use in sense or antisense suppression of one or more cell cycle genes in a host cell, tissue, or plant. Attachment of chemical agents that bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated cell cycle genes from a cDNA library prepared from insertion sequence mutagenized plants. Progeny seed from the plants comprising the desired inactivated gene can be grown to a plant to study the phenotypic changes characteristic of that inactivation. See, Tools to Determine the Function of Genes, 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the cell cycle polypeptides (e.g., preproenzyme, proenzyme, or enzymes) as disclosed herein. The present invention also provides proteins comprising at least one epitope from a cell cycle polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of cell cycle polypeptides.

The isolated nucleic acids of the present invention can be used over a broad range of plant types, including species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea,* and

*Populus.* Preferred plants include corn, soybeans, sorghum, sunflower, wheat, rice, alfalfa and canola.

Nucleic Acids

The present invention provides, inter alia, isolated nucleic acids of RNA, DNA, and analogs and/or chimeras thereof, comprising a cell cycle polynucleotide.

A. Polynucleotides Encoding a Protein of SEQ ID NOS: 2, 12, 14, or 22 or Conservatively Modified or Polymorphic Variants Thereof The present invention provides isolated heterologous nucleic acids comprising a cell cycle polynucleotide, wherein the polynucleotide encodes a cell cycle polypeptide, disclosed herein in SEQ ID NOS: 2, 12, 14, or 22, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 11, 13, or 21, and silent variations of polynucleotides encoding a polypeptide of SEQ ID NOS: 2, 12, 14, or 22. The present invention further provides isolated nucleic acids comprising polynucleotides encoding conservatively modified variants of a polypeptide of SEQ ID NOS: 2, 12, 14, or 22. Conservatively modified variants can be used to generate or select antibodies immunoreactive to the non-variant polypeptide.

B. Polynucleotides Amplified from a *Zea mays* Nucleic Acid Library

As indicated in (b), supra, the present invention provides isolated nucleic acids comprising cell cycle polynucleotides, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.).

The nucleic acid library may be a cDNA library, a genomic library, or a library generally constructed from nuclear transcripts at any stage of intron processing. Generally, a cDNA nucleic acid library will be constructed to comprise a majority of full-length cDNAs. Often, cDNA libraries will be normalized to increase the representation of relatively rare cDNAs.

Total RNA Isolation: Libraries can be made from a variety of maize tissues but for optimal results one should isolate RNA's from mitotically active tissues such as shoot meristems, shoot meristem cultures, callus and suspension cultures, immature ears and tassels, and young seedlings. Since cell cycle proteins are typically expressed at specific cell cycle stages it may be possible to enrich for such rare messages using exemplary cell cycle inhibitors such as aphidicolin, hydroxyurea, mimosine, and double-phosphate starvation methods to block cells at the G1/S boundary. Cells can also be blocked at this stage using the double phosphate starvation method. Hormone treatments that stimulate cell division, for example cytokinin, would also increase expression of the cell cycle RNA.

Full length cDNA libraries from such rapidly-dividing tissues (or cells at the G1/S boundary) would provide opportunities for identifying full length, cell cycle related cDNAs. Full length cDNA libraries can be constructed using the "Biotinylated CAP Trapper" method (Carninci, P., et al., *Genomics* 37:327-336, 1996) or the "mRNA Cap Retention Procedure" (Edery, I., et al., *Molecular and Cellular Biology* 15:3363-3371, 1995). Full length cDNA libraries can be normalized to provide a higher probability of sampling genes that express at low levels. Examples of cDNA library normalization methods are summarized by Bento Soares (Bonaldo, M. F., et al., *Genome Research* 6:791-806, 1996).

Functional fragments of cell cycle protein can be identified using a variety of techniques such as restriction analysis, Southern analysis, primer extension analysis, and DNA sequence analysis. Function can also be determined by complementing yeast strains known to be mutant for G1 cell cycle proteins with maize homologs. Primer extension analysis or S1 nuclease protection analysis, for example, can be used to localize the putative start site of transcription of the cloned gene. Ausubel at pages 4.8.1 to 4.8.5; Walmsley et al., "Quantitative and Qualitative Analysis of Exogenous Gene Expression by the S1 Nuclease Protection Assay," in Methods in Molecular Biology, Vol. 7, *Gene Transfer and Expression.*

The general approach of such functional analysis involves subcloning DNA fragments of a genomic clone, cDNA clone or synthesized gene sequence into an expression vector, introducing the expression vector into a heterologous host, and relying on an assay system such as BrdU incorporation to monitor DNA synthesis in conjunction with various well-established visual methods to follow cell division (e.g. see T. Motomura, Cell cycle analysis in a multinucleate green alga, *Boergensia forbesti* (*Syphonoclades, Chlorophyta*). *Phycological Res.* 44(1):11-17, and J. L. Kennard et al., Pre-mitotic nuclear migration in subsidiary mother cells of Tradescantia occurs in the G1 of the cell cycle. *Cell Motility and the Cytoskeleton* 36:55-67). Methods for generating fragments of a cDNA or genomic clone are well known. In addition, variants can be obtained, for example, by oligonucleotide-directed mutagenesis, linker-scanning mutagenesis, mutagenesis using the polymerase chain reaction, and the like. See, for example, Ausubel, pages 8.0.3-8.5.9. Also, see generally, McPherson (ed.), *Directed Mutagenesis: A Practical Approach*, (IRL Press, 1991). Thus, the present invention also encompasses DNA molecules comprising nucleotide sequences that have substantial sequence similarity with SEQ ID NO: 1, 11, 13, or 22 and encode CycD.

The polynucleotides of the present invention include those amplified using the following primer pairs:

```
Primer sets for ZmCycDa-1
1) Primer sets flanking ZmCycDa-1 cDNA:
Set #1:
SEQ ID NO: 3    For01 5' GCAAGCATGGTGCCGGGCTATGACTGC 3'

SEQ ID NO: 4    Rev01 5' AGCGGTGAGGAGCACACCTGAAGCGTACCA 3'

Set #2:
SEQ ID NO: 3    For01 5' GCAAGCATGGTGCCGGGCTATGACTGC 3'

SEQ ID NO: 5    Rev02 5' TCTATTCCTCTGCCGACCCCCATCCTT 3'
```

-continued

```
Set #3:
SEQ ID NO: 6      For02 5' CCCCTCTCCACTTGAGAAGAACACAATTAG 3'

SEQ ID NO: 4      Rev01 5' AGCGGTGAGGAGCACACCTGAAGCGTACCA 3'

Set #4:
SEQ ID NO: 6      For02 5' CCCCTCTCCACTTGAGAAGAACACAATTAG 3'

SEQ ID NO: 5      Rev02 5' TCTATTCCTCTGCCGACCCCCATCCTT 3'

2) Primer sets inside ZmCycDa-1 cDNA:
Set #1:
SEQ ID NO: 7      For01 5' CGGGCTATGACTGCGCCGCCTCCGT 3'

SEQ ID NO: 8      Rev01 5' CTCCTCTTGCTTGTGGAAGAACTATGG 3'

Set #2:
SEQ ID NO: 9      For02: 5' ATGGTGCCGGGCTATGACTGCGCCG 3'

SEQ ID NO: 10     Rev02: 5' TTAGAGTAGACGTCTAGTGATCCTT 3'

Primer sets for ZmCycDb-1:
1) Primer sets inside ZmCycDb-1:
Set #1
SEQ ID NO: 15     For01: 5' CACGCGCACCAGCCCACCGCCCAG 3'

SEQ ID NO: 16     Rev01: 5' TCCCATCGGATCTCCTCTAGCGCCC 3'

Primer sets for ZmCycDc-1:
1) Primer sets flanking ZmCycDc-1 cDNA:
Set #1:
SEQ ID NO: 23     For01: CAGTACCCCCACGCTGCACAG SEQ ID NO: 24     Rev01: TCACGCTTGTTCTGTCGTCTTTACAC Set #2:
SEQ ID NO: 25     For02: GCTGCTGCAAGTCCGCAACCACTG SEQ ID NO: 26     Rev02: CGCTTGTTCTGTCGTCTTTACACTG 2) Primer sets inside ZmCycDc-1 cDNA:
Set #1:
SEQ ID NO: 27     For01: 5' ACCTCCATCCTCATCTGCCTGGAAGAC SEQ ID NO: 28     Rev01: 5' CTGGACTGCACTGCACTGCAATGC Set #2:
SEQ ID NO: 29     For02: 5' CATCCTCATCTGCCTGGAAGACGGC SEQ ID NO: 30     Rev02: 5' AATGCACTGCCAGCAGCTGAGCT
```

The present invention also provides subsequences of full-length nucleic acids. Any number of subsequences can be obtained by reference to SEQ ID NOS: 1, 11, 13, or 21, and using primers which selectively amplify, under stringent conditions to: at least two sites to the polynucleotides of the present invention, or to two sites within the nucleic acid which flank and comprise a polynucleotide of the present invention, or to a site within a polynucleotide of the present invention and a site within the nucleic acid which comprises it. A variety of methods for obtaining 5' and/or 3' ends is well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28-38.); see also, U.S. Pat. No. 5,470,722, and Current Protocols in Molecular Biology, Unit 15.6, Ausubel, et al., Eds., Greene Publishing and Wiley-Interscience, New York (1995). Thus, the present invention provides cell cycle polynucleotides having the sequence of the cell cycle gene, nuclear transcript, cDNA, or complementary sequences and/or subsequences thereof.

Primer sequences can be obtained by reference to a contiguous subsequence of a polynucleotide of the present invention. Primers are chosen to selectively hybridize, under PCR amplification conditions, to a polynucleotide of the present invention in an amplification mixture comprising a genomic and/or cDNA library from the same species. Generally, the primers are complementary to a subsequence of the amplicon they yield. In some embodiments, the primers will be constructed to anneal at their 5' terminal end's to the codon encoding the carboxy or amino terminal amino acid residue (or the complements thereof) of the polynucleotides of the present invention. The primer length in nucleotides is selected from the group of integers consisting of from at least 15 to 50. Thus, the primers can be at least 15, 18, 20, 25, 30, 40, or 50 nucleotides in length. A non-annealing sequence at the 5' end of the primer (a "tail") can be added, for example, to introduce a cloning site at the terminal ends of the amplicon.

The amplification primers may optionally be elongated in the 3' direction with additional contiguous nucleotides from the polynucleotide sequences, such as SEQ ID NOS: 1, 11, 13, or 21, from which they are derived. The number of nucleotides by which the primers can be elongated is selected from the group of integers consisting of from at least 1 to 25. Thus, for example, the primers can be elongated with an additional 1, 5, 10, or 15 nucleotides. Those of skill will recognize that a lengthened primer sequence can be employed to increase specificity of binding (i.e., annealing) to a target sequence.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes that are specific to a polypeptide of the present invention. Methods for protein synthesis from PCR derived templates are known in the art and available commercially. See, e.g., Amersham Life Sciences, Inc., Catalog '97, p. 354.

C. Polynucleotides Which Selectively Hybridize to a Polynucleotide of (A) or (B)

As indicated in (c), supra, the present invention provides isolated nucleic acids comprising cell cycle polynucleotides, wherein the polynucleotides selectively hybridize, under selective hybridization conditions, to a polynucleotide of paragraphs (A) or (B) as discussed, supra. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated from a *Zea mays* nucleic acid library. Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having at Least 60% Sequence Identity with the Polynucleotides of (A), (B) or (C)

As indicated in (d), supra, the present invention provides isolated nucleic acids comprising cell cycle polynucleotides, wherein the polynucleotides have a specified identity at the nucleotide level to a polynucleotide as disclosed above in paragraphs (A), (B), or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will share an epitope with a polypeptide encoded by the polynucleotides of (A), (B), or (C). Thus, these polynucleotides encode a first polypeptide that elicits production of antisera comprising antibodies that are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences that can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), supra, the present invention provides isolated nucleic acids comprising cell cycle polynucleotides, wherein the polynucleotides encode a protein having a subsequence of contiguous amino acids from a prototype cell cycle polypeptide. Exemplary prototype cell cycle polypeptides are provided in SEQ ID NOS. 2, 12, 14, or 23. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as, but not limited to, a polypeptide encoded by the polynucleotide of (b), supra, or exemplary polypeptides of SEQ ID NOS. 2, 12, 14, or 23. Generally, however, a protein encoded by a polynucleotide of this embodiment does not bind to antisera raised against the prototype polypeptide when the antisera have been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera that is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated cell cycle polypeptides as disclosed herein. Molecular weight can be readily determined by SDS-PAGE under reducing conditions. Preferably, the molecular weight is within 15% of a full-length cell cycle polypeptide, more preferably within 10% or 5%, and most preferably within 3%, 2%, or 1% of a full-length cell cycle polypeptide of the present invention. Molecular weight determination of a protein can be conveniently performed by SDS-PAGE under denaturing conditions.

Optionally, the polynucleotides of this embodiment will encode a protein having a specific activity at least 20%, 30%, 40%, or 50% of the native, endogenous (i.e., non-isolated), full-length cell cycle polypeptide. Further, the proteins encoded by polynucleotides of this embodiment will optionally have a substantially similar apparent dissociation constant ($K_m$) and/or catalytic activity (i.e., the microscopic rate constant, $k_{cat}$) as the native endogenous, full-length cell cycle protein. Those of skill in the art will recognize that $k_{cat}/K_m$ value determines the specificity for competing substrates and is often referred to as the specificity constant. Proteins of this embodiment can have a $k_{cat}/K_m$ value at least 10% of the non-isolated full-length cell cycle polypeptide as determined using the substrate of that polypeptide from the cell cycle specific pathways, supra. Optionally, the $k_{cat}/K_m$ value will be at least 20%, 30%, 40%, 50%, and most preferably at least 60%, 70%, 80%, 90%, or 95% the $k_{cat}/K_m$ value of the non-isolated, full-length cell cycle polypeptide. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)-(E)

As indicated in (f), supra, the present invention provides isolated nucleic acids comprising cell cycle polynucleotides, wherein the polynucleotides are complementary to the polynucleotides of paragraphs A-E, above. As those of skill in the art will recognize, complementary sequences base-pair throughout the entirety of their length with the polynucleotides of (A)-(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides that are Subsequences of the Polynucleotides of (A)-(F)

As indicated in (g), supra, the present invention provides isolated nucleic acids comprising cell cycle polynucleotides, wherein the polynucleotide comprises at least 15 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype sequence, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequence compounds that bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is *Zea mays*. Particularly preferred is the use of *Zea mays* tissue from tassel and vegetative meristem.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is generally a vector, adapter, or linker for cloning and/or expression of a polynucleotide of the present invention. Use of cloning vectors, expression vectors, adapters, and linkers is well known in the art. Exemplary nucleic acids include such vectors as: M13, lambda ZAP Express, lambda ZAP II, lambda gt10, lambda gt11, PBK-CMV, PBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, PSPUTK, p3'SS, POPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc., Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. While isolation of RNA and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as: Stratagene, and Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., the Stratagene lambda ZAP Express (cDNA cloning vector with 0 to 12 kb cloning capacity).

An exemplary method of constructing a greater than 95% pure full-length cDNA library is described by Carninci et al., *Genomics* 37:327-336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.* 15(6):3363-3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705-5711 (1990); Patanjali et al., Proc. Natl. Acad. U.S.A. 88:1943-1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude, *Proc. Natl. Acad. Sci. USA* 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, Technique, 3(2):58-63 (1991); Sive and St. John, Nucl. Acids Res., 16(22):10937 (1988);

*Current Protocols in Molecular Biology*, Ausubel, et al., Eds., Greene Publishing and Wiley-Interscience, New York (1995); and, Swaroop et al., *Nucl. Acids Res.,* 19(8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual,* 2nd Ed., Cold Spring Harbor Laboratory, Vols. 1-3 (1989), *Methods in Enzymology,* Vol. 152, *Guide to Molecular Cloning Techniques,* Berger and Kimmel, Eds., San Diego: Academic Press, Inc. (1987), *Current Protocols in Molecular Biology,* Ausubel, et al., Eds., Greene Publishing and Wiley-Interscience, New York (1995); *Plant Molecular Biology: A Laboratory Manual,* Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to clone flanking genomic sequences, 5' untranslated regions and 3' sequences, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481-486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68:90-99 (1979); the phosphodiester method of Brown et al., *Meth. Enzymol.* 68:109-151 (1979); the diethylphosphoramidite method of Beaucage et al., *Tetra. Lett.* 22:1859-1862 (1981); the solid phase phosphoramidite triester method described by Beaucage and Caruthers, *Tetra. Letts.* 22(20): 1859-1862 (1981), e.g., using an automated synthesizer, e.g., as described in Needham-VanDevanter et al., *Nucleic Acids Res.,* 12:6159-6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

Cell cycle vectors were constructed using standard molecular biology techniques. See, for example, Sambrook et al. (eds.) *Molecular Cloning: a Laboratory Manual*, Second Edition, (Cold Spring Harbor Laboratory Press, cold Spring Harbor, N.Y. 1989). Plasmids are based on pUC18. The vectors used in these experiments contain combinations of the same basic regulatory elements. The Omega prime (O') 5-prine sequence is described by Gallie et al., *Nucl. Acids Res.* 15:3257-3273 (1987). The selective marker gene, bar (Thompson et al., *EMBO J.* 6:2519-2523 (1987)), was used in conjunction with bialaphos selection to recover transformants. The Cauliflower Mosaic Virus 35S promoter with a duplicated enhancer region is described by Gardner et al., *Nucl. Acid Res.* 9:2871-2888 (1981). The 79 bp Tobacco Mosaic Virus leader is described by Gallie et al., *Nucl. Acid Res.* 15:3257-3273 (1987) and was inserted downstream of the promoter followed by the first intron of the maize alcohol dehydrogenase gene ADH1-S. Described by Dennis et al., *Nucl. Acid Res.* 12:3983-3990 (1984). The 3' sequence pinII is described by An et al., *Plant Cell* 1:115-122 (1989).

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Promoters

A. Inducible Promoters

An inducible promoter can be operably linked to a nucleotide sequence encoding ZmCycD. Optionally, the inducible promoter is operably linked to a nucleotide sequence encoding a signal sequence which is operably linked to a nucleotide sequence encoding ZmCycD. With an inducible promoter the rate of transcription increases in response to an inducing agent.

Any inducible promoter can be used in the instant invention. See Ward et al., Plant Mol. Biol. 22:361-366 (1993). Exemplary inducible promoters include that from the ACE1 system which responds to copper (Mett et al., *PNAS* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., Mol. Gen. Genet. 227:229-237 (1991). A particularly preferred inducible promoter is a promoter that responds to an inducing agent to which plants do not normally respond. An exemplary inducible promoter is the inducible promoter from a steroid hormone gene the transcriptional activity of which is induced by a glucocorticosteroid hormone. Schena et al., *Proc. Natl. Acad. Sci. U.S.A.* 88:10421 (1991).

The expression vector comprises an inducible promoter operably linked to a nucleotide sequence encoding ZmCycD. The expression vector is introduced into plant cells and presumptively transformed cells are exposed to an inducer of the inducible promoter. The cells can be screened for the presence of ZmCycD protein by northern, RPA, or RT-PCR (using transgene specific probes/oligo pairs) BrdU or cell division assays, as described above.

B. Tissue-Specific or Tissue Preferred Promoters

A tissue-specific promoter can be operably linked to a nucleotide sequence encoding a ZmCycD protein. Optionally, the tissue-specific promoter is operably linked to a nucleotide sequence encoding a signal sequence which is operably linked to a nucleotide sequence encoding ZmCycD. Plants transformed with a gene encoding ZmCycD operably linked to a tissue-specific promoter produce the ZmCycD protein exclusively, or preferentially, in a specific tissue.

Any tissue-specific or tissue-preferred promoter can be utilized in the instant invention. Exemplary tissue-specific or tissue-preferred promoters include a seed-preferred promoter such as that from the phaseolin gene (Murai et al., *Science* 23:476-482 (1983) and Sengupta-Gopalan et al., *Proc. Natl. Acad. Sci. USA* 82:3320-3324 (1985)), napin promoter, β-conglycinin promoter soybean lectin promoter, maize 15 kD zein promoter, 22 kD zein promoter, γ-zein promoter, waxy promoter, shrunken 1 promoter, globulin 1 promoter and shrunken 2 promoter (Thompson, et al.; *BioEssays*; Vol. 10; p. 108; (1989); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genet.* 217:240-245 (1989)); a pollen-specific promoter such as that from Zm13 (Guerrero et al., *Mol. Gen. Genet.* 224:161-168 (1993)) or a microspore-preferred promoter such as that from apg (Twell et al., *Sex. Plant Reprod.* 6:217-224 (1993)).

The expression vector comprises a tissue-specific or tissue-preferred promoter operably linked to a nucleotide sequence encoding cell cycle protein. The expression vector is introduced into plant cells. The cells are screened for the presence of cell cycle protein by either BrdU or cell division assays, as described above.

C. Constitutive Promoters

A constitutive promoter can be operably linked to a nucleotide sequence encoding a cell cycle protein or the constitutive promoter is operably linked to a nucleotide sequence encoding a signal sequence which is operably linked to a nucleotide sequence encoding cell cycle protein.

Many different constitutive promoters can be utilized in the instant invention. Exemplary constitutive promoters include the promoters from plant viruses such as the 35S promoter from CaMV (Odell et al., *Nature* 313:810-812 (1985)), *Commelina* yellow mottled virus (R. Torbert et al., *Plant Cell Rep.* 17:284-287 (1988)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genet.* 231:276-285 (1992) and Atanassova et al., *Plant Journal* 2(3):291-300 (1992)).

The ALS promoter, a XbaI/NcoI fragment 5-prime to the *Brassica napus* ALS3 structural gene (or a nucleotide sequence that has substantial sequence similarity to the XbaI/NcoI fragment), represents a particularly useful constitutive promoter. Co-pending Pioneer Hi-Bred International U.S. patent application Ser. No. 08/409,297.

The expression vector comprises a constitutive promoter operably linked to a nucleotide sequence encoding cell cycle protein. The expression vector is introduced into plant cells and presumptively transformed CELLS are screened for the presence of cell cycle protein by either BrdU or cell division assays, as described above.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter cell cycle content and/or composition in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cell cycle gene so as to control the expression of the gene. Gene expression can be modulated under conditions suitable for plant growth so as to alter cell cycle content and/or composition. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114-115, Freeling and Walbot, Eds., Springer, N.Y. (1994); *Corn and Corn Improvement*, $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; DNA probe arrays; and isolation of proteins known to be expressed with some specificity in the target tissue. Such methods are well known to those of skill in the art. Commercially available products for identifying promoters are known in the art such as the Clontech (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5-10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, N.Y. (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221-227 (1983). In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., *Meth. In Enzymol.* 153:253-277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene* 61:1-11 (1987) and Berger et al., *Proc. Natl. Acad. Sci. U.S.A.* 86:8402-8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. USA* 85:8805-8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., The Plant Cell 2:279-289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., Nucleic Acids Res. (1986) 14:4065-4076, describe covalent bonding of a single-stranded DNA fragment with alkylating derivatives of nucleotides complementary to target sequences. A report of similar work by the same group is that by Knorre, D. G., et al., *Biochimie* (1985) 67:785-789. Iverson and Dervan also showed sequence-specific cleavage of single-stranded DNA mediated by incorporation of a modified nucleotide which was capable of activating cleavage (*J. Am. Chem. Soc.* (1987) 109:1241-1243). Meyer, R. B., et al., *J. Am. Chem. Soc.* (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197-3203. Use of crosslinking in triple-helix forming probes was also disclosed by Home, et al., *J. Am. Chem. Soc.* (1990) 112:2435-2437. Use of N4,N4-ethanocytosine as an alkylating agent to crosslink to single-stranded oligonucleotides has also been described by Webb and Matteucci, *J. Am. Chem. Soc.* (1986) 108:2764-2765; *Nucleic Acids Res.* (1986) 14:7661-7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NOS: 2, 12, 14, or 22. The proteins of the present invention or variants thereof can comprise any number of contiguous amino acid residues from a polypeptide of the present invention, wherein that number is selected from the group of integers consisting of from 10 to the number of residues in a full-length cell cycle polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NOS: 2, 12, 14, or 22. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so. In eukaryotic cells overexpression of a non-functional fusion protein may be desirable. After isolation and purification of the fusion protein from the expressing cells, enzymatic cleavage could be used to restore function to the purified CycD protein. In addition, fusions with CycD can have application for affinity matrices and affinity columns used for purifying other cell cycle genes. For example, "His-patch" thioredoxin fusions can be expressed, and the isolate His-CycD fusion protein bound to metal chelate columns. Whole cell protein extracts can then be passed through the column to selectively trap proteins that interact with CycD. See Ausubel et al., 1990 for general methods. Similarly, glutathione-S transferase fusions can be used to attach proteins to solid-phase matrices for this type of affinity binding. This method has been used, for example, to identify cell cycle genes whose proteins bind to GST-Rb in L. Magnaghi-Jaulin et al., Retinoblastoma protein represses transcription by recruiting a histone deacetylase. Nature 391: 601-604 (1998). It may also be advantageous to fuse additional functional genes to the CycD gene. For example it would be useful to fuse a green fluorescent gene or some other reporter gene.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible) followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in E. coli is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al., Gene 22:229-235 (1983); Mosbach et al., Nature 302:543-545 (1983)).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein et al., *Gene* 8:17-24 (1979); Broach et al., *Gene* 8:121-133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cell cultures. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider, *J. Embryol. Exp. Morphol.* 27:353-365 (1987)).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-781 (1983)). Additionally, gene sequences to control replication in the host cell may be incorporated into the vector such as those found in bovine papilloma virus type-vectors. Saveria-Campo, M., *Bovine Papilloma Virus DNA a Eukaryotic Cloning Vector in DNA Cloning* Vol. II a Practical Approach, D. M. Glover, Ed., IRL Press, Arlington, Va., pp. 213-238 (1985).

Use in Two-Hybrid Systems

An important utility for the maize CycD genes that have been cloned in the genetic approach of using a two-hybrid system to identify interacting proteins (i.e. proteins that specifically interact with the CycD gene-encoded products. This method, typically done using the yeast *Saccharomyces cerevisiae*, exploits the fact that a functional transcription factor can be separated into two components; a DNA-binding factor and an activation domain, which when held together non-covalently will still bind DNA and activate transcription. The test system is constructed as follows: a DNA-binding domain is localized 5' to a reporter gene, for example luciferase, and this cassette is transformed into a yeast strain. The nucleic acid sequence for the DNA-binding domain of the transcriptional factor is ligated to the gene (or partial gene sequence) being used as bait. Expression of this DNA-binding domain-bait fusion is driven, for example by the yeast adh1 promoter. A "library" of gene-fusions is also produced, using the activation domain of the transcriptional factor fused to genes (or gene fragments) from an expression library of interest (referred to as the activation domain hybrid). Expression of the activation domain hybrids is also accomplished, for example, using the yeast adh1 promoter. To perform the two-hybrid screen, plasmids encoding the DNA-binding domain hybrid and a library of activation domain hybrids are introduced (sequentially or simultaneously) into a yeast strain already containing the inactive reporter. Transformed yeast in which the activation domain hybrid specifically bind to the DNA-binding domain hybrid will express luciferase. Positives are further characterized by sequence analysis, and further tests of relevance of biological interactions.

Commonly used DNA-binding domains include those from lexA protein in *E. coli*, and the Ga14 protein in yeast. Likewise, commonly used activation domains include B42 (bacterial) and Ga14 (yeast). For details, see Hannon G, and Bartel P, *Identification of interacting proteins using the two-hybrid system, Methods Mol. Cellular Biol.* 5:289-297 (1995).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

Gene Transformation Methods

Numerous methods for introducing foreign genes into plants are known and can be used to insert the cell cycle gene into a plant host, including biological and physical plant transformation protocols. See, for example, Miki et. al., 1993, "Procedure for Introducing Foreign DNA into Plants," In: *Methods in Plant Molecular Biology and Biotechnology*, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., *Science* 227:1229-31, 1985), electroporation, micro-injection, and biolistic bombardment.

Expression cassettes and vectors and in vitro culture methods for plant cell or tissue transformation and regeneration of plants are known and available. See, for example, Gruber et. al., 1993, "Vectors for Plant Transformation" In: *Methods in*

*Plant Molecular Biology and Biotechnology*, Glick and Thompson, eds., CRC Press, Inc., Boca Raton, pages 89-119.

Agrobacterium-Mediated Transformation

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, 1991, *Crit. Rev. Plant Sci.* 10:1. Descriptions of the *Agrobacterium* vector systems and methods for *Agrobacterium*-mediated gene transfer are provide in Gruber et al., supra; Miki et al., supra; and Moloney et al., 1989, *Plant Cell Reports* 8:238.

Direct Gene Transfer

Methods for *Agrobacterium*-mediated transformation in rice is disclosed in (Hiei et. al., 1994, *The Plant Journal* 6:271-282) and maize (Ishida et al., 1996, *Nature/Biotechnology* 14:745-750). Several methods of plant transformation, collectively referred to as direct gene transfer, have been developed as an alternative to *Agrobacterium*-mediated transformation. Methods for *Agrobacterium*-mediated transformation in sorghum are disclosed in WO 98/49332. Methods for *Agrobacterium*-mediated transformation in maize are disclosed in WO 98/32326.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes. (Sanford et al., 1987, *Part. Sci. Technol.* 5:27; Sanford, 1988, *Trends Biotech* 6:299; Sanford, 1990, Physiol. Plant 79:206; Klein et al., 1992, *Biotechnology* 10:268).

Another method for physical delivery of DNA to plants is sonication of target cells as described in Zang et al., 1991, *Bio/Technology* 9:996. Alternatively, liposome or spheroplast fusions have been used to introduce expression vectors into plants. See, for example, Deshayes et al., 1985, *EMBO J.* 4:2731; and Christou et al., 1987, *PNAS USA* 84:3962. Direct uptake of DNA into protoplasts using $CaCl_2$ precipitation, polyvinyl alcohol or poly-L-ornithine have also been reported. See, for example, Hain et al., 1985, *Mol. Gen. Genet.* 199:161; and Draper et al., 1982, *Plant Cell Physiol.* 23:451.

Electroporation of protoplasts and whole cells and tissues has also been described. See, for example, Donn et al., 1990, In: *Abstracts of the VIIth Int'l Congress on Plant Cell and Tissue Culture (IAPTC)*, A2-38, page 53; D'Halluin et al., 1992, *Plant Cell* 4:1495-1505; and Spencer et al., 1994, *Plant Mol. Biol.* 24:51-61. Microinjection of DNA into whole plant cells has also been described as has microinjection into protoplasts. See, for example in whole cells, Neuhaus et al., 1987, *Theor. Appl. Genet.* 75:30-36; and in protoplasts, Crossway et al., 1986, *Mol. Gen. Genet.* 202:179-185; and Reich et al., 1986, *Biotechnology* 4:1001-1004.

Particle Wounding/Agrobacterium Delivery

Another useful basic transformation protocol involves a combination of wounding by particle bombardment, followed by use of *Agrobacterium* for DNA delivery, as described by Bidney et al., *Plant Mol. Biol.* 18:301-313 (1992). Useful plasmids for plant transformation include PHP9762. The binary backbone for PHP9762 is bin 19. See Bevan, *Nucleic Acids Research* 12:8711-8721 (1984).

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with cefotaxime (plus kanamycin for the NPTII selection). Selection can also be done using kanamycin.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime (plus kanamycin for selection).

Transfer by Plant Breeding

Once a single transformed plant has been obtained by the foregoing recombinant DNA method, e.g., a plant transformed with a desired gene, conventional plant breeding methods can be used to transfer the structural gene and associated regulatory sequences via crossing and backcrossing. In general, such plant breeding techniques are used to transfer a desired gene into a specific crop plant. In the instant invention, such methods include the further steps of: (1) sexually crossing a transformed plant with a second non-transformed plant; (2) recovering reproductive material from the progeny of the cross; and (3) growing transformed containing plants from the reproductive material.

Isolated nucleic acid acids of the present invention can be introduced into plants according techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22:421-477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

The introduction of DNA constructs using polyethylene glycol precipitation is described in Paszkowski et al., Embo J. 3:2717-2722 (1984). Electroporation techniques are described in Fromm et al., *Proc. Natl. Acad. Sci.* 82:5824 (1985). Ballistic transformation techniques are described in Klein et al., *Nature* 327:70-73 (1987).

*Agrobacterium tumefaciens-meditated* transformation techniques are well described in the scientific literature. See, for example Horsch et al., *Science* 233:496-498 (1984), and Fraley et al., *Proc. Natl. Acad. Sci.* 80:4803 (1983). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: *Genetic Engineering*, vol. 6, P W J Rigby, Ed., London, Academic Press, 1987; and Lichtenstein, C. P., and Draper, J., In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25:1353, 1984), (3) the vortexing method (see, e.g., Kindle, *Proc. Natl. Acad. Sci. USA* 87:1228, (1990)).

DNA can also be introduced into plants by direct DNA transfer into pollen as described by Zhou et al., *Methods in Enzymology* 101:433 (1983); D. Hess, *Intern Rev. Cytol.*, 107:367 (1987); Luo et al., *Plane Mol. Biol. Reporter* 6:165 (1988). Expression of polypeptide coding genes can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo* 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis*, pp. 3-284 in *The Peptides: Analysis, Synthesis, Biology*. Vol. 2: *Special Methods in Peptide Synthesis, Part A*.; Merrifield et al., *J. Am. Chem. Soc.* 85:2149-2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture*, Handbook of Plant Cell Culture, Macmillilan Publishing Company, New York, pp. 124-176 (1983); and *Binding, Regeneration of Plants, Plant Protoplasts*, CRC Press, Boca Raton, pp. 21-73 (1985).

Transformed plant cells, calli or explant can be cultured on regeneration medium in the dark for several weeks, generally about 1 to 3 weeks to allow the somatic embryos to mature. Preferred regeneration media include media containing MS salts, such as PHI-E and PHI-F media. The plant cells, calli or explant are then typically cultured on rooting medium in a light/dark cycle until shoots and roots develop. Methods for plant regeneration are known in the art and preferred methods are provided by Kamo et al., (*Bot. Gaz.* 146(3):324-334, 1985), West et al., (*The Plant Cell* 5:1361-1369, 1993), and Duncan et al. (*Planta* 165:322-332, 1985).

Small plantlets can then be transferred to tubes containing rooting medium and allowed to grow and develop more roots for approximately another week. The plants can then be transplanted to soil mixture in pots in the greenhouse.

The regeneration of plants containing the foreign gene introduced by *Agrobacterium* from leaf explants can be achieved as described by Horsch et al., *Science* 227:1229-1231 (1985). In this procedure, transformants are grown in the presence of a selection agent and in a medium that induces the regeneration of shoots in the plant species being transformed as described by Fraley et al., Proc. Natl. Acad. Sci. U.S.A. 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467-486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered cell cycle content or composition).

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

Modulating Cell Cycle Protein Content and/or Composition

The present invention further provides a method for modulating (i.e., increasing or decreasing) cell cycle protein content or composition in a plant or part thereof. Modulation can be effected by increasing or decreasing the cell cycle protein content (i.e., the total amount of cell cycle protein) and/or the cell cycle protein composition (the ratio of various cell cycle monomers in the plant) in a plant. The method comprises transforming a plant cell, transiently or stably, with a recombinant expression cassette comprising a polynucleotide of the present invention as described above to obtain a transformed plant cell. For stably transformed plant cells, growing the transformed plant cell under plant forming conditions, and inducing expression of a polynucleotide of the present invention in the plant for a time sufficient to modulate cell cycle protein content and/or composition in the plant or plant part.

In some embodiments, plant cell division may be modulated by altering, in vivo or in vitro, the promoter of a non-isolated cell cycle gene to up- or down-regulate gene expression. In some embodiments, the coding regions of native cell cycle genes can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate cell cycle protein content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra.

Induction of expression of a polynucleotide of the present invention can also be controlled by exogenous administration of an effective amount of inducing compound. Inducible promoters and inducing compounds that activate expression from these promoters are well known in the art. In preferred embodiments, cell division is modulated in monocots, particularly maize.

Molecular Markers

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a cell cycle gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a cell cycle gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of the genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387-395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J. H., et al. *Proc. Natl. Acad. Sci. USA* 94:4504-4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a cell cycle gene or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-cell cycle genes that would yield a false positive result.

Detection of the hybridization complex can be achieved using any number of well-known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic acid in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3):230-250 (1986); Haase et al., *Methods in Virology*, Vol. VII, pp. 189-226 (1984); Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule that is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally-occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K., A Colorimetric Method for DNA Hybridization, *Nucl. Acids Res.* 12:3435-3444 (1984)) and synthetic oligonucleotides have been coupled directly with alkaline phosphatase (Jablonski, E., et al., Preparation of Oligodeoxynucleotide-Alkaline Phosphatase Conjugates and Their Use as Hybridization Probes, *Nuc. Acids. Res.* 14:6115-6128 (1986); and Li P., et al., Enzyme-linked Synthetic Oligonucleotide probes: Non-Radioactive Detection of Enterotoxigenic *Escherichia Coli* in Faeca Specimens, *Nucl. Acids Res.* 15:5275-5287 (1987)).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Persons of skill know many methods of making antibodies. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native cell cycle protein of 5 amino acids in length or greater and selected from a protein encoded by a polynucleotide of the present invention are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quaternary structure. Naturally occurring cell cycle polypeptides can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$-$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495-497 (1975). Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse et al., *Science* 246:1275-1281 (1989); and Ward et al., *Nature* 341:544-546 (1989); and Vaughan et al., *Nature Biotechnology*, 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845-851 (1996). Also, recombinant immunoglobulins may be produced. See, Cabilly, U.S. Pat. No. 4,816,567; and Queen et al., *Proc. Natl. Acad. Sci.* 86:10029-10033 (1989).

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance that provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well-recognized immunological binding assays (see, e.g., U.S. Pat. Nos. 4,366,241; 4,376,110; 4,517,288; and 4,837,168). For a review of the general immunoassays, see also *Methods in Cell Biology*, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, *Practice and Theory of Enzyme Immunoassays, Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval et al., *J. Immunol.* 111: 401-1406 (1973), and Akerstrom et al., *J. Immunol.* 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for Use in Immunoassays

A protein that specifically binds to or that is specifically immunoreactive with an antibody generated against a defined immunogen, such as an immunogen consisting of the amino acid sequence of SEQ ID NOS: 2, 12, 14, or 22, is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorbtion prior to use in the immunoassay (e.g., by immunoabsorbtion of the antisera with a protein of different substrate specificity (e.g., a different enzyme) and/or a protein with the same substrate specificity but of a different form).

In order to produce antisera for use in an immunoassay, a polypeptide is isolated as described herein. For example, recombinant protein can be produced in a mammalian or other eukaryotic cell line. An inbred strain of mice is immunized with the protein of using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570-573. Preferably, two or more distinct forms of polypeptides are used in this determination. These distinct types of polypeptides are used as competitors to identify antibodies that are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and colorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the activity of active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length cell cycle polypeptide (e.g., enzyme). Generally, the polypeptide will be present in a range sufficient to determine the effect of the compound, typically about 1 nM to 10 μM. Likewise, the compound will be present in a concentration of from about 1 nM to 10 μM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics are well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

Clones of ZmCycDa-1 and ZmCycDc-1 are on deposit with the American Type Culture Collection (ATCC). The ATCC is at 10801 University Boulevard, Manassas, Va. 20110-2209. The deposits have been made under the terms of the Budapest Treaty and given the ATCC designation 98848 and 98847 respectively.

During the pendency of this patent application, access to the deposited cultures will be available to the Commissioner of Patents and Trademarks and to persons determined by the Commissioner to be entitled thereto under 37 CFR 1.14 and 35 U.S.C. 122.

All restrictions imposed by the depositor on the availability to the public of the deposited material will be irrevocably removed upon the granting of a patent. However, it should be understood that the availability of a deposit does not constitute a license to practice the subject invention in derogation of patent rights granted by government action.

EXAMPLES

Example 1

Isolation of Maize CycD Genes

Total RNA was isolated from corn tissues with TRizol Reagent (Life Technology Inc. Gaithersburg, Md.) using a modification of the guanidine isothiocyanate/acid-phenol procedure described by Chomczynski and Sacchi [Chomczynski, P., and Sacchi, N., *Anal. Biochem.* 162, 156 (1987)]. In brief, plant tissue samples were pulverized in liquid nitrogen before the addition of the TRizol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation:

The selection of poly(A)+ RNA from total RNA was performed using PolyATract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed using high stringency conditions and eluted using RNase-free deionized water.

cDNA Library Construction:

cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between Not I and Sal I sites. Mitotically active tissues from *Zea mays* were employed, including such sources as shoot cultures, immature inflorescences (tassel and ear) as well as other sources of vegetative meristems.

Sequencing Template Preparation:

Individual colonies were picked and DNA was prepared either by PCR with M13 forward primers and M13 reverse primers, or by plasmid isolation. All the cDNA clones were initially sequenced using M13 reverse primers. As additional fragments of the genes were discovered, new sequencing primers were designed.

PROTOCOLS, Murray (ed.), pages 271-281 (Humana Press, Inc. 1991). Functional fragments of the cell cycle protein are identified by their ability, upon introduction to cells, to stimulate the G1 to S-phase transition, which is manifested by increased DNA replication in a population of cells and by increased cell division rates.

5'-RACE

Library RACE was performed using several of Pioneer's maize libraries. 5' RACE was done using a cDNA library constructed from leaves and stems of maize plants at the three-leaf stage. The principal of 5' RACE is described in detail in numerous publications such as: Frohman M. A. 1993. Rapid Amplification of Complementary DNA Ends for Generation of Full-Length Complementary DNAs: Thermal RACE. In: Methods in Enzymology, vol. 28, pp 340-356. Detailed procedure can be found in the ClonTech Marathon cloning manual.

Example 2

Using CycD's in a Two-Hybrid System to Identify Maize Cell Cycle Genes

CycD gene expression during the G1→S transition and early S-phase play a prominent role in progression through the cell cycle. The proteins encoded by the CycD gene family are a critical part of the complex that binds and phosphorylates retinoblastoma-associated gene family members. In turn, Rb releases E2F and this transcription factor starts the cascade of events leading to DNA replication. As such, the CycD genes and their encoded proteins can be used to identify other cell cycle regulatory proteins. This can be done using the CycD gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). Using this method, *Zea mays* Cdc2, Cdk4 and Rb genes are identified as components of the activation domain hybrid, and are confirmed through further sequence analysis. Similarly, inhibitors of the Cdk4/CycD complex such as CIP and Ink are identified.

Example 3

CycD-Bound Affinity Columns for Identifying Cdk4 Proteins and their Encoding Genes Purified recombinant CycD protein can be immobilized on a matrix via a covalent crosslinking or affinity purification as described supra. This matrix can then be used to pull-down proteins that interact with CycD proteins, inter alia, cyclin-dependent kinase. CDK activity can then be assessed by measuring the addition of radioactive phosphorus to protein-substrates and CDK protein levels determined by immunoassay. Additionally, this can be used to purify the CDK activity present in different plant tissues and protein fractions. The presence and level of other CycD interacting proteins can also be determined on the basis of immunological assay, activity quantification, SDS-PAGE analysis and other methods. These measures can then be correlated with the reproductive state, capacity for division, developmental stage, or the quality of different samples. A CycD nucleic acid can also be adducted to a second nucleic acid sequence encoding a DNA-binding domain in order to identify CycD interacting proteins.

Example 4

Transient CycD Expression Stimulates DNA Replication and Enhances Transgene Integration Regardless of the method of DNA delivery, cells competent for the integration of foreign DNA must be actively dividing. There is a growing body of evidence suggesting that integration of foreign DNA occurs in dividing cells (this includes both *Agrobacterium* and direct DNA delivery methods). It has long been observed that dividing transformed cells represent only a fraction of cells that transiently express a transgene. It is well known (in non-plant systems) that the delivery of damaged DNA, (similar to what we introduce by particle gun delivery methods) induces an immediate cell cycle arrest, a process involving cyclin dependent kinase inhibitors (CDKI's). This inhibition can be obviated by ectopic transient over-expression of positive cell cycle regulators or by down-regulation of negative regulators. Regardless of the mechanism of arrest; i.e. presence of damaged DNA or delivery into a non-cycling differentiated cell, stimulation of the cell cycle will increase integration frequencies. To demonstrate this, the CycD gene is cloned into a cassette with a constitutive promoter (i.e. either a strong maize promoter such as the ubiquitin promoter including the first ubiquitin intron, or a weak constitutive promoter such as nos). Delivery of the ZmCycD gene in an appropriate plant expression cassette (for example, in a UBI::ZmCycD::pinII-containing plasmid) along with UBI::bar::pinII can be accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. Using one of the above methods, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids. Transient expression of the CycD gene overcomes the G1/S checkpoint controls, and increases the proportion of recipient-cells (i.e. into which DNA was introduced) that enter S-phase. This stimulation through the G1/S transition in cells harboring transgenic plasmid DNA provides an optimal cellular environment for integration of the introduced genes. Cytological methods can be used to verify increased frequencies of progression through S-phase and mitosis (i.e. for cells in which a visual marker such as GFP was transformed alongside CycD the green fluorescent cells will exhibit a higher mitotic index). Cells in S-phase (undergoing DNA replication) can be monitored by detecting nucleotide analog incorporation. For example, following incubation of cells with bromodeoxyuridine (BrdU) incorporation of this thymadine analog can be detected by methods such as antiBrdU immunocytochemistry or through enhancement of Topro3 fluorescence following BrdU labeling. It is expected that CycD expression will increase the proportion of cells incorporating BrdU (i.e. a higher percentage of transformed cells will incorporate BrdU relative to untransformed cells). Increased DNA synthesis can also be monitored using such methods as fluorescence activated cell sorting (FACS) of protoplasts (or nuclei), in conjunction with appropriate BrdU-insensitive fluorescent DNA labels such as propidium iodide and DAPI or BrdU-detecting methods described above. For example, tissue is homogenized to release nuclei that are analyzed using the FACS for both green fluorescence (from our accompanying GFP marker) and DNA content. Such FACS analysis can demonstrate that expression of a co-transformed GFP reporter correlates with CycD-induced changes in the ratios of cells in G1, S and G2. Similar experiments can be run using the fluorescently labeled anti-BrdU antisera to demonstrate that CycD expression increased the percentage of cells in S-phase. Cell cycle stage-specific probes can also be used to monitor cell cycle progression. For example, numerous spindle-associated proteins are expressed during a fairly narrow window during mitosis, and antibodies or nucleic acid probes to cyclins, histones, or DNA synthesis enzymes can be used as positive markers for the G1/S transition. For cells that have received the CycD gene cassette, stimulation of the cell cycle is manifested in an increased mitotic index, detected by staining for mitotic figures using a DNA dye such as DAPI or Hoechst 33258. FACS analysis of CycD-expressing cells is expected to show that a high percentage of cells have progressed into or through S-phase. Progression through S-phase will be manifested by fewer cells in G1 and/or more rapid cycling times (i.e. shorter G1 and G2 stages). A higher percentage of cells are labeled when cell cycle stage-specific probes are used, as mentioned above.

To assess the effect on transgene integration, growth of bialaphos-resistant colonies on selective medium is a reliable assay. Within 1-7 days after DNA introduction, the embryos are moved onto culture medium containing 3 mg/l of the selective agent bialaphos. Embryos, and later callus, are transferred to fresh selection plates every 2 weeks. After 6-8 weeks, transformed calli are recovered. Transgenic callus containing the introduced genes can be verified using PCR and Southern analysis. Northern analysis can also be used to verify which calli are expressing the bar gene, and whether the CycD gene is being expressed at levels above normal wild-type cells (based on hybridization of probes to freshly isolated mRNA population from the cells). In immature embryos that had transient, elevated CycD expression, higher numbers of stable transformants are recovered (likely a direct result of increased integration frequencies). Increased transgene integration frequency can also be assessed using such well-established labeling methods such as in situ hybridization.

For this specific application (using transient CycD-mediated cell cycle stimulation to increase transient integration frequencies), it may be desirable to reduce the likelihood of ectopic stable expression of the CycD gene. Strategies for transient-only expression can be used. This includes delivery of RNA (transcribed from the CycD gene) or CycD protein along with the transgene cassettes to be integrated to enhance transgene integration by transient stimulation of cell division. Using well-established methods to produce CycD-RNA, this can then be purified and introduced into maize cells using physical methods such as microinjection, bombardment, electroporation or silica fiber methods. For protein delivery, the gene is first expressed in a bacterial or baculoviral system, the protein purified and then introduced into maize cells using physical methods such as microinjection, bombardment, electroporation or silica fiber methods. Alternatively, CycD proteins are delivered from *Agrobacterium tumefaciens* into plant cells in the form of fusions to *Agrobacterium* virulence proteins. Fusions are constructed between CycD and bacterial virulence proteins such as VirE2, VirD2, or VirF which are known to be delivered directly into plant cells. Fusions are constructed to retain both those properties of bacterial virulence proteins required to mediate delivery into plant cells and the CycD activity required for enhancing transgene integration. This method should ensure a high frequency of simultaneous co-delivery of T-DNA and functional CycD protein into the same host cell. The methods above represent various means of using the CycD gene or its encoded product to transiently stimulate DNA replication and cell division, which in turn enhances transgene integration by providing an improved cellular/molecular environment for this event to occur.

Example 5

Altering CycD Expression Stimulated the Cell Cycle, Increasing Integration and Growth Based on results in other eukaryotes, expression of ZmCycD genes stimulates the G1/S transition and promotes cell division. This increase in division rate is assessed in a number of different manners, more rapid incorporation of radiolabeled nucleotides, and faster growth (i.e. more biomass accumulation). Delivery of the ZmCycD in an appropriate plant expression cassette is accomplished through numerous well-established methods for plant cells, including for example particle bombardment, sonication, PEG treatment or electroporation of protoplasts, electroporation of intact tissue, silica-fiber methods, microinjection or *Agrobacterium*-mediated transformation. The result of ZmCycD gene expression will be to stimulate the G1/S transition and hence cell division, providing the optimal cellular environment for integration of introduced genes (as per Example 1). This will trigger a tissue culture response (cell divisions) in genotypes that typically do not respond to conventional culture techniques, or stimulate growth of transgenic tissue beyond the normal rates observed in wild-type (non-transgenic) tissues. To demonstrate this, the CycD gene (ZmCycDc-1) was cloned into a cassette with a constitutive promoter (the ubiquitin promoter, UBI, including the first ubiquitin intron). Particle bombardment was used to introduce the UBI::ZmCycDc-1::pinII-containing plasmid along with a UBI::PAT~GFP::pinII-containing plasmid (which, when expressed produced a functional PAT~GFP fusion protein which confered bialaphos resistance and green fluorescence) into maize cells capable of growth on suitable maize culture medium. Such competent cells can be from maize suspension culture, callus culture on solid medium, freshly isolated immature embryos or meristem cells. Immature embryos of the Hi-II genotype were used as the target for co-delivery of these two plasmids. Ears were harvested at approximately 10 days post-pollination, and 1.2-1.5 mm immature embryos were isolated from the kernels. The immature embryos were bombarded from 18-72 hours later. Typically, the immature embryos were placed on a high-osmoticum medium for 6-18 hours prior to bombardment, and were left on this medium for an additional 18 hours after bombardment.

DNA Particle Bombardment

Between 6 and 18 hours prior to bombardment, the immature embryos were placed on medium with additional osmoticum (MS basal medium, Musashige and Skoog, 1962, *Physiol. Plant* 15:473-497, with 0.25 M sorbitol). The embryos on the high-osmotic medium were used as the bombardment target.

For particle bombardment, plasmid DNA (described above) was precipitated onto 1.8 μm tungsten particles using standard CaCl$_2$-spermidine chemistry (see, for example, Klein et al., 1987, *Nature* 327:70-73). Each plate was bombarded once at 600 PSI, using a DuPont Helium Gun (Lowe et al., 1995, *Bio/Technol* 13:677-682). For typical media formulations used for maize immature embryo isolation, callus initiation, callus proliferation and regeneration of plants, see Armstrong, C. 1994. In "The Maize Handbook", M. Freeling and V. Walbot, eds. Springer Verlag, NY, pp 663-671.

Selection

Within 1-7 days the embryos were moved onto N6-based culture medium containing 3 mg/l of the selective agent bialaphos. Embryos, and later callus, were transferred to fresh selection plates every 2 weeks. After the first 14 days post-bombardment, the calli developing from the immature embryos were screened for GFP expression using an epifluorescent dissecting-microscope. Typically, (i.e. in the absence of a cell cycle gene) this is too early to observe growing multicellular transformants. Instead, as typical after such a short post-bombardment duration, numerous GFP-expressing single-cells were observed on control embryos (where the UBI::PAT~GFP::pinII plasmid was introduced alone), but GFP-expressing multicellular clusters were not observed. In marked contrast to the control treatment, when UBI::CycDc-1 was included along with the PAT~GFP marker, numerous GFP+ multicellular clusters were observed growing from the immature embryos at this same early time-point. This early stimulation and higher number of growing transformants observed in the CycD treatment, suggest that expression of this cell cycle gene increased integration frequencies (thus higher numbers) and stimulated growth of these small colonies after integration had occurred (thus, the transformants were clearly visible at this early juncture). After 6-8 weeks, transformed calli were recovered. In treatments where both the PAT~GFP gene and CycD were transformed into immature embryos, a higher number of growing calli were recovered on the selective medium and callus growth was stimulated (relative to treatments with the bar gene alone). In the first comparative experiments of this type, immature embryos were harvested from 30 ears (over a period of 3 months). From each ear, 25 embryos were used for the control and 25 embryos were used for the UBI::CycD treatment. Thus the total number of embryos used per treatment was 750. The transformation frequency (the number of transgene-expressing independent calli relative to the starting number of embryos) for the control treatment was 2.4%. For the UBI::CycDc-1 treated embryos, the transformation frequency had increased to 7.2%.

A second experiment demonstrated that both the maize CycDa-1 and CycDc-1 genes result in increased transformation frequencies relative to the control treatment (where the cyclin gene was not included). For this bombardment experiment (performed in a similar manner to that described above), 3 Hi-II ears were harvested at 10 DAP, and the immature embryos were divided evenly between the 3 treatments (125 embryos per treatment). Again, transformants appeared at earlier timepoints in the two CycD treatments and the final number of transformants in the CycD treatments was substantially higher. When screened for GFP expression 46 days post-bombardment, no GFP-expressing multicellular calli were observed in the control treatment, while in the CycDc-1 and CycDa-1 treatments there were macroscopic GFP+ calli at frequencies of 0.7 and 2.3%, respectively. After 77 days, the overall transformation frequency for the control was 7.4%, while for CycDc-1 and CycDa-1 the frequency had increased to 12.0 and 18.3% respectively. In addition, the calli in the CycD treatments were substantially larger than in the control treatment, indicating that these genes stimulated growth rates.

Differences in cell cycle profiles were also observed in CycD-expressing cells relative to control (wild-type) cells. To demonstrate that overexpression of CycD genes could accelerate cell division, the cell cycle profile of maize calli expressing Ubi::CycD were analyzed using a cell sorter (flow cytometry assay). Flow cytometry is a standard method to study cell cycle, using procedures that are well established in the literature, as, for example, in Sonea I M et al., *Am J Vet Res.* 1999 60(3):346-53. Briefly, by counting the number of cells that are in G1 phase versus the number of cells that are in G2 phase, one can estimate, in a given population, the percentage of cells that are undergoing cell division. The higher the percentage of cells in G1 phase, the less the number of cells that are dividing. Under standard culture conditions, approximately 70% of the G1/G2 cells of maize calli are in the G1 phase. In maize calli expressing CycD genes, alterations of the distribution of cells in the G1 and G2 phases were observed. In 14 out of 19 CycDa-1 expressing events, the proportion of cells in G1 phase decreased to below 60%, and in some cases dropped below 30%. Thus, in these 14 CycDa-1 events, more cells were undergoing cell division compared to wild type maize calli. Using a different CycD gene also altered the cell cycle of transformants, but not in as many events. Compared to the 14 out of 19 CycDa-1 expressing events with increased cell division rates, only two out of 32 CycDc-1 expressing events showed that the percentage of G1 cells was lower than 60%. In control calli expressing similar vector genes but lacking a CycD gene, the cell cycle profile remained similar to that of the non-treated wild type maize calli.

Calli from both the CycDa-1 and CycDc-1 treatment regenerated easily. Healthy, fertile transgenic plants were grown in the greenhouse. Seed-set on CycD transgenic plants was similar to control plants, and transgenic progeny were recovered.

For a given CycD gene, it was also observed that higher expression levels improved transformation. For this bombardment experiment (performed in a similar manner to that described above), 3 Hi-II ears were harvested at 10 DAP, and the immature embryos were divided evenly between the 3 treatments (125 embryos per treatment). The treatments included a no-cyclin control (UBI::PAT~GFP::pinII), or the UBI::PAT~GFP::pinII marker plus one of three cyclin-expressing plasmids (UBI::CycDc-1, nos::CycDc-1 or UBI::Da-1). For the CycDc-1 gene, this experiment compared high levels of cyclin expression (UBI) to low levels (nos). The transformation frequency in the control treatment was 3.0%. When expression was driven by the UBI promoter, the transformation frequencies for the CycDa-1 and CycDc-1 genes were 14.4 and 17.6%, respectively. However, placing the CycDc-1 gene behind the nos promoter resulted in a transformation similar to the control (1.6%). Based on this result, it appears that higher expression levels result in correspondingly higher recovery of transformants.

Example 6

Identifying Transformants in the Absence of Chemical Selection

When the CycD gene is introduced without any additional selective marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are expressing the maize CycD gene at levels above normal wild-type cells (based on hybridization of probes to freshly isolated mRNA population from the cells).

Inducible Expression:

The CycD gene can also be cloned into a cassette with an inducible promoter such as the benzenesulfonamide-inducible promoter. The expression vector is co-introduced into plant cells and after selection on bialaphos, the transformed cells are exposed to the safener (inducer). This chemical induction of CycD expression should result in stimulated G1/S transition and more rapid cell division. The cells are screened for the presence of ZmCycD RNA by northern, or RT-PCR (using transgene specific probes/oligo pairs), for CycD-encoded protein using CycD-specific antibodies in Westerns or using hybridization. Increased DNA replication is detected using BrdU labeling followed by antibody detection of cells that incorporated this thymidine analogue. Likewise, other cell cycle division assays could be employed, as described above.

Example 7

Control of CycD Gene Expression Using Tissue-Specific or Cell-Specific Promoters Provides a Differential Growth Advantage CycD gene expression using tissue-specific or cell-specific promoters stimulates cell cycle progression in the expressing tissues or cells. For example, using a seed-specific promoter will stimulate cell division rate and result in increased seed biomass. Alternatively, driving CycD expression with a strongly-expressed, early, tassel-specific promoter will enhance development of this entire reproductive structure.

Expression of CycD genes in other cell types and/or at different stages of development will similarly stimulate cell division rates. Similar to results observed in *Arabidopsis* (Doerner et al., 1996), root-specific or root-preferred expression of CycD will result in larger roots and faster growth (i.e. more biomass accumulation).

Example 8

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival. Transformation of an apical initial with a Cyclin D expression cassette under the expression of a promoter active in the apical meristem (either meristem specific or constitutive) would allow the transformed cells to grow faster and displace wildtype initials driving the meristem towards homogeneity and minimizing the chimeric nature of the plant body. To demonstrate this, the CycD gene is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see Lowe et al., 1997). The cyclin D expression cassette along with a reporter construct such as Ubi:GUS:pinII can then be co-delivered (preferably 24 hours after isolation) into the exposed apical dome using conventional particle gun transformation protocols. As a control the CycD construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the CycD gene in meristem cells, through stimulation of the G1→S transition, will result in greater integration frequencies and hence more numerous transgenic sectors. Integration and expression of the CycD gene will impart a competitive advantage to expressing cells resulting in a progressive enlargement of the transgenic sector. Due to the enhanced growth rate in CycD-expressing meristem cells, they will supplant wild-type meristem cells as the plant continues to grow. The result will be both enlargement of transgenic sectors within a given cell layer (i.e. periclinal expansion) and into adjacent cell layers (i.e. anticlinal invasions). As an increasingly large proportion of the meristem is occupied by CycD-expressing cells, the frequency of CycD germline inheritance should go up accordingly.

Example 9

Use of Flp/Frt System to Excise the CycD Cassette

In cases where the CycD gene has been integrated and CycD expression is useful in the recovery of maize trangenics, but is ultimately not desired in the final product, the CycD expression cassette (or any portion thereof that is flanked by appropriate FRT recombination sequences) can be excised using FLP-mediated recombination (see U.S. patent application Ser. No. 08/972,258 filed Nov. 18, 1997).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for increasing transformation frequency of a maize cell comprising introducing into a maize cell an isolated cyclin D (CycD) polynucleotide operably linked to a promoter; wherein said CycD polynucleotide encodes a polypeptide comprising at least 95% sequence identity to SEQ ID NO: 14 and wherein the % identity is determined by GCG/bestfit program using a gap creation penalty of 50 and a gap extension penalty of 3; wherein when a maize CycD polypeptide is expressed from said CycD polynucleotide, said maize cell has increased transformation efficiency when compared to a maize cell without an introduced isolated CycD polynucleotide; and wherein said maize CycD polypeptide binds to cyclin-dependent kinase 4 (CDK4).

2. The method of claim 1, wherein said CycD polynucleotide encodes SEQ ID NO: 14.

3. The method of claim 1, wherein said CycD polynucleotide is SEQ ID NO: 13.

4. An isolated nucleic acid encoding a polypeptide which increases transformation frequency in a maize cell comprising:

(a) a polynucleotide encoding a polypeptide comprising at least 95% sequence identity to SEQ ID NO: 14, wherein the % identity is determined by GCG/bestfit program using a gap creation penalty of 50 and a gap extension penalty of 3;

(b) a polynucleotide encoding SEQ ID NO: 14;

(c) a polynucleotide of SEQ ID NO: 13; or, (d) a polynucleotide fully complementary to a polynucleotide of (a), (b), or (c).

5. A recombinant expression cassette comprising the nucleic acid of claim 4 operably linked to a promoter.

6. A host cell comprising the nucleic acid of claim 4 stable incorporated in its genome.

7. The host cell of claim 6, wherein the host cell is a plant cell.

8. The host cell of claim 7, wherein the host cell is selected from the group consisting of corn, soybean, sorghum, sunflower, safflower, wheat, rice, alfalfa, or *Brassica* cell.

9. The host cell of claim 6, wherein the host cell is in a plant.

10. The host cell of claim 9, wherein the plant is selected from the group consisting of corn, soybean, sorghum, sunflower, safflower, wheat, rice, alfalfa, or *Brassica*.

11. The host cell of claim 6, wherein the host cell is in a seed.

12. The host cell of claim 11, wherein the seed is from a plant selected from the group consisting of corn, soybean, sorghum, sunflower, safflower, wheat, rice, alfalfa, or *Brassica*.

* * * * *

UNITED STATES PATENT AND TRADEMARK OFFICE
CERTIFICATE OF CORRECTION

PATENT NO. : 7,799,566 B2 Page 1 of 1
APPLICATION NO. : 11/560550
DATED : September 21, 2010
INVENTOR(S) : Lowe et al.

It is certified that error appears in the above-identified patent and that said Letters Patent is hereby corrected as shown below:

Column 97, Line 5 replace "stable" with "stably"

Signed and Sealed this

Thirtieth Day of November, 2010

David J. Kappos
*Director of the United States Patent and Trademark Office*